United States Patent [19]
Schulte et al.

[11] Patent Number: 5,797,924
[45] Date of Patent: Aug. 25, 1998

[54] STEREOTACTIC FIXATION SYSTEM AND CALIBRATION PHANTOM

[75] Inventors: Reinhard W. Schulte, Grand Terrace; William J. Wicks, Redondo Beach; Helmut J. Meinass, Grand Terrace, all of Calif.

[73] Assignee: Loma Linda University Medical Center, Loma Linda, Calif.

[21] Appl. No.: 610,354

[22] Filed: Mar. 4, 1996

Related U.S. Application Data

[60] Division of Ser. No. 344,291, Nov. 22, 1994, Pat. No. 5,549,616, which is a continuation-in-part of Ser. No. 148,213, Nov. 2, 1993, Pat. No. 5,464,411.

[51] Int. Cl.⁶ ................................................ A61B 19/00
[52] U.S. Cl. ................................................ 606/130; 606/1
[58] Field of Search ............................... 606/1, 130, 116; 604/116

[56] References Cited

U.S. PATENT DOCUMENTS

| | | |
|---|---|---|
| 1,202,971 | 10/1916 | Daiber . |
| 4,270,531 | 6/1981 | Blachly et al. . |
| 4,550,713 | 11/1985 | Hyman . |
| 4,583,949 | 4/1986 | Heartness . |
| 4,591,341 | 5/1986 | Andrews . |
| 4,602,622 | 7/1986 | Bar et al. . |
| 4,841,965 | 6/1989 | Jacobs . |
| 4,917,344 | 4/1990 | Prechter et al. . |
| 4,971,060 | 11/1990 | Schneider et al. . |
| 5,039,057 | 8/1991 | Prechter et al. . |
| 5,090,047 | 2/1992 | Angotti et al. . |
| 5,094,241 | 3/1992 | Allen . |
| 5,107,839 | 4/1992 | Houdek et al. . |
| 5,117,829 | 6/1992 | Miller et al. . |
| 5,207,688 | 5/1993 | Carol . |
| 5,221,283 | 6/1993 | Chang . |
| 5,230,623 | 7/1993 | Guthrie et al. . |
| 5,242,455 | 9/1993 | Skeens et al. ............... 606/130 |
| 5,260,581 | 11/1993 | Lesyna et al. . |
| 5,269,305 | 12/1993 | Corol . |
| 5,281,232 | 1/1994 | Hamilton et al. . |

FOREIGN PATENT DOCUMENTS 2213066A   9/1989   United Kingdom .

OTHER PUBLICATIONS

The Laitinen Stereoadapter: Application to the fractionated stereotactic irradiation of the brain; Delannes et al., Neurochirurgie, 1990, 36:167–175 (in French with English translation).

A halo–ring technique for fractionated stereotactic radiotherapy; Clark et al., The British Journal of Radiology, 1993, 66, 522–527.

Proton Treatment Center Newsletter, vol. 2, No. 4, Oct. 1992, Loma Linda University Medical Center.

*Primary Examiner*—Glenn K. Dawson
*Attorney, Agent, or Firm*—Knobbe, Martens, Olsen & Bear, LLP

[57] ABSTRACT

A stereotactic fixation apparatus provides for accurate and reproducible positioning of a patient's skull during medical diagnostic and treatment procedures. The stereotactic fixation apparatus includes a mouthpiece having an acrylic impression formed as an impression of the patient's upper teeth and hard palate. The mouthpiece is connected to a stereotactic frame, which in turn is releasable connected to an adaptor board on which the patient rests. Vacuum pressure is used to draw the acrylic impression firmly against the patient's hard palate. Vacuum pressure is also used to hold the stereotactic frame on the adaptor board. The stereotactic fixation apparatus additionally includes a patient-activated safety release mechanism which allows the patient to disconnect the vacuum pressure and to dislodge the restraints of the mouthpiece and frame, as well as to disable the medical equipment used with the medical diagnostic or treatment procedure. A calibration phantom desirably is used with the stereotactic fixation apparatus to calibrate the orientation of the mouthpiece relative to the reference axes of the medical treatment device during each stage of the patient's course.

22 Claims, 11 Drawing Sheets

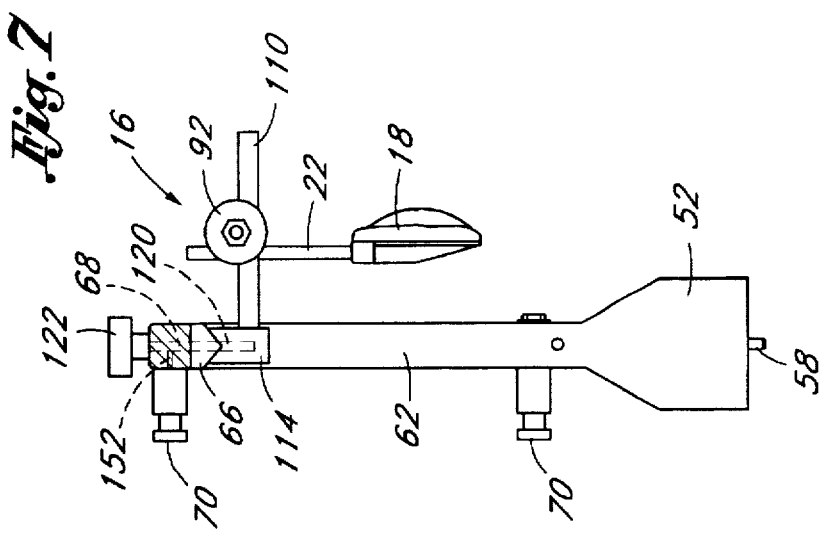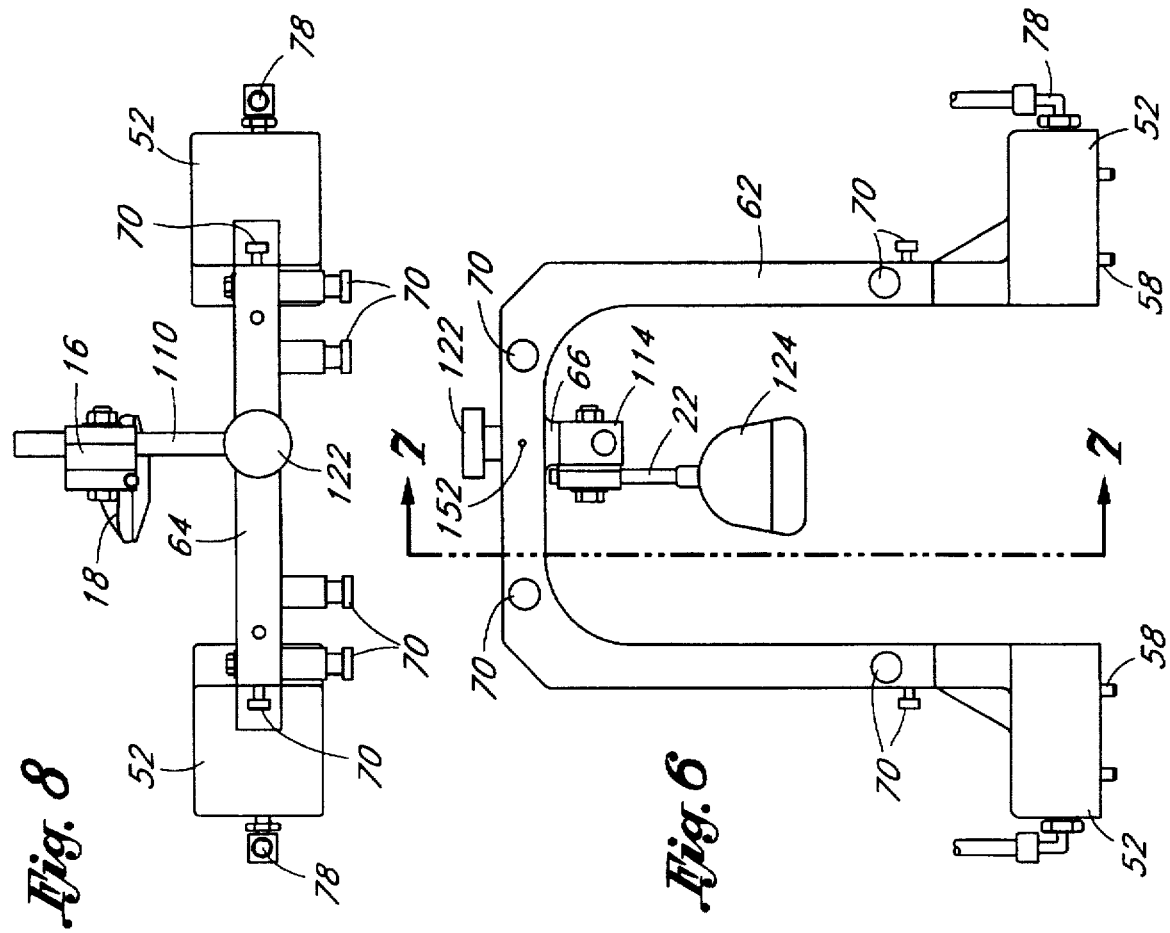

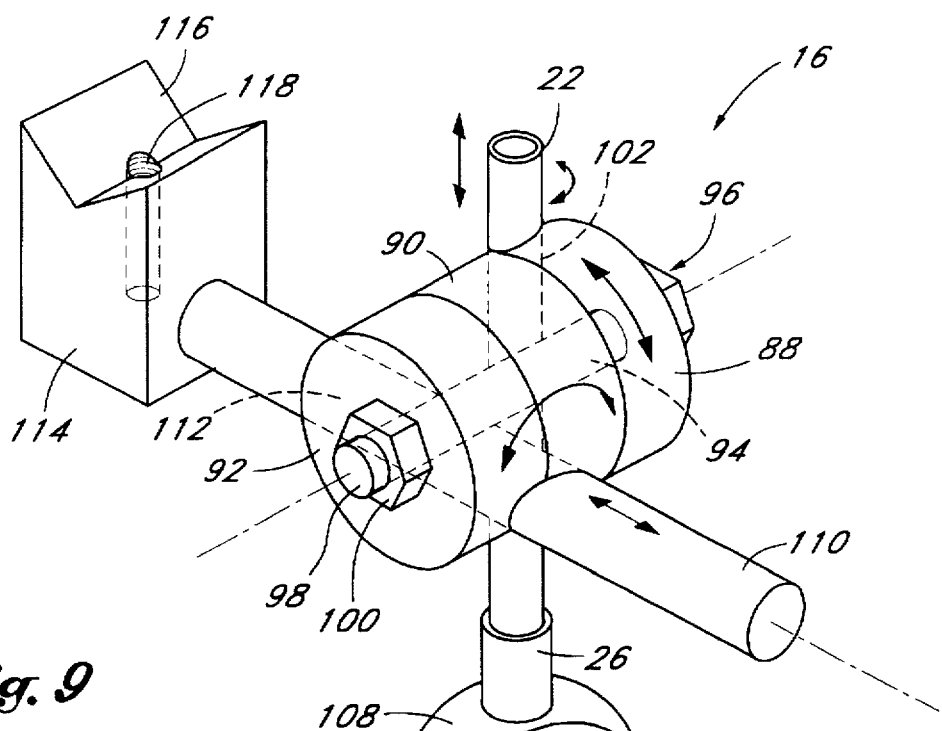
Fig. 9
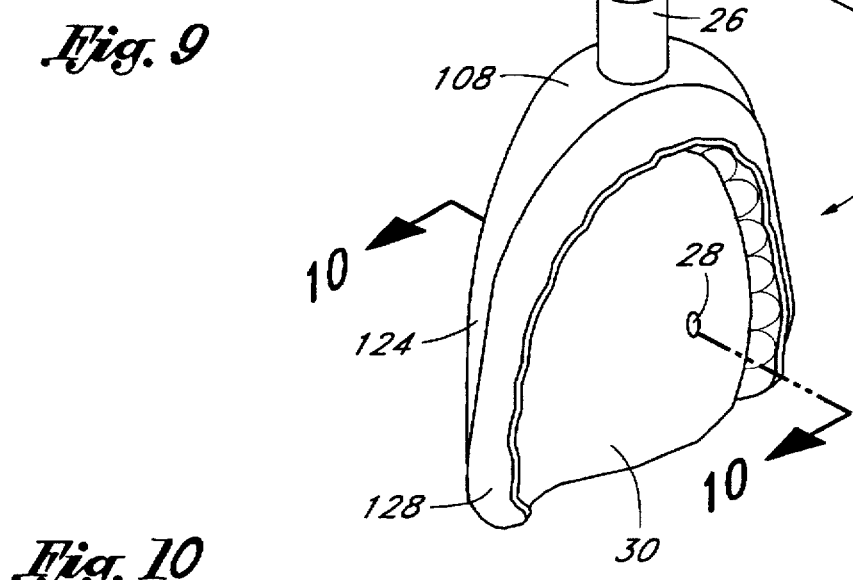
Fig. 10
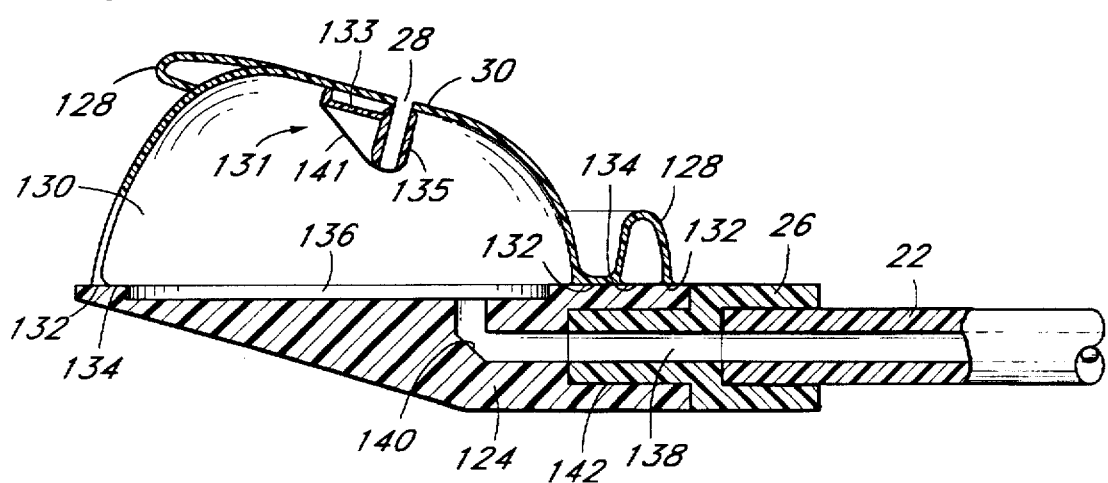

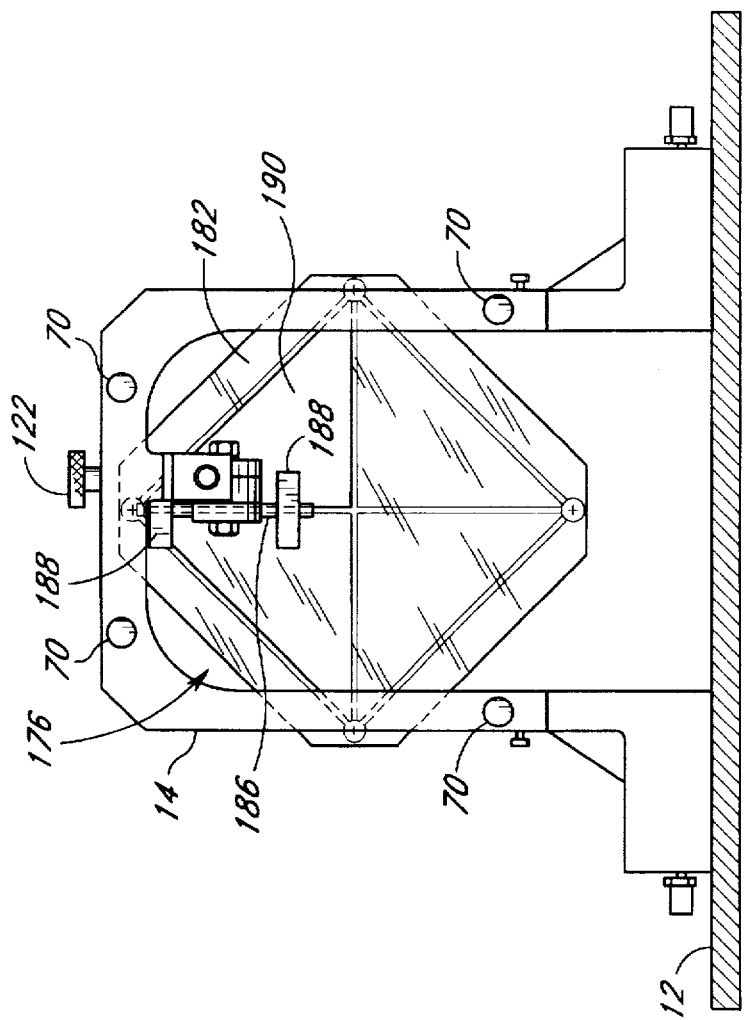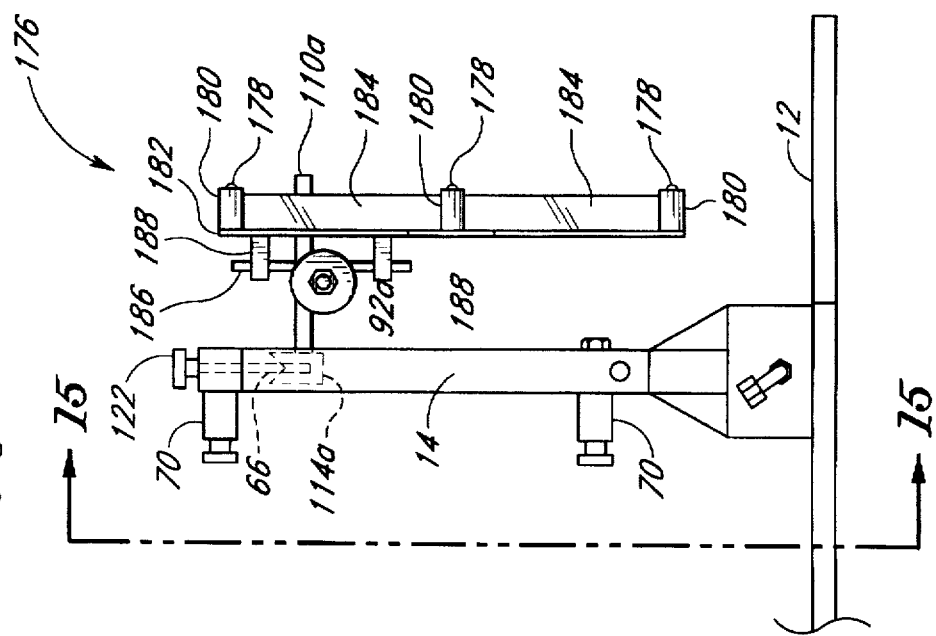

STEREOTACTIC FIXATION SYSTEM AND CALIBRATION PHANTOM

RELATED CASE

This application is a divisional of U.S. patent application Ser. No. 08/344,291, filed Nov. 22, 1994, now U.S. Pat. No. 5,549,616, which is a continuation-in-part of application Ser. No. 08/148,213, filed Nov. 2, 1993, now U.S. Pat. No. 5,464,411.

BACKGROUND OF THE INVENTION

1. Field of the Invention

The present invention relates to a system for immobilizing a patient's skull during a medical diagnostic or treatment procedure, and more particularly to a stereotactic fixation system which permits precise and reproducible positioning of the patient's skull for focal irradiation or like medical procedures.

2. Description of Related Art

Modern methods of imaging, such as computerized tomography and magnetic resonance imaging, enable radiation oncologist to precisely delineate volumes of diseased tissue and normal anatomical structures. The data from imaging scans makes it possible to tailor radiation doses to a particular, identifiable treatment volume.

Focal radiation treatment usually involves the use of external beams, such as, for example, photon or proton beams. Such treatment requires accurate positioning and immobilization of the patient because a small misalignment in a patient's position with respect to the external beam can result in missing the target and/or delivering the high dose of radiation to normal, non-targeted tissue. The distance from the high-dose region of the external beam to its lateral and distal edges is often but millimeters.

Radiation treatment and pretreatment diagnostic studies also require reproducible positioning of the patient. Radiotherapy typically involves several diagnostic, planning and treatment stages. At each stage subsequent to the initial, accurate repositioning of the patient is essential. Most patients also require multiple treatments extending over several weeks. Variation of the treatment position between different sessions will decrease the efficacy of the treatment.

In an effort to provide accurate and reproducible positioning of a patient, stereotactic location devices have been developed. These devices rely on the assumption that the skull and its contents are rigid. Each anatomic point within the skull can then be uniquely identified when one knows the three spacial coordinates of that anatomic point.

Original neurosurgical and radiosurgical stereotactic location devices typically attach to the patient's skull by three or four pins surgically affixed. These invasive devices cannot be removed between diagnostic studies and treatment procedures, which therefore have to be performed within one day.

More recently, a relocatable stereotactic location device has been developed which employs a halo-ring which is invasively attached to the patient's skull and remains in place for several weeks unless the treatment is finished. An example of these devices is described in Clark, B. G., et al., "A Halo-Ring Technique for Fractionated Stereotactic Radiotherapy," *The British Journal of Radiation*, pp. 522–527 (June 1993). Such devices, however, are still invasive and may cause discomfort to the patient.

Another prior relocatable stereotactic device is described in Delannes, M., et al., "The Laitinen Stereoadaptor," *Neurochirurgie*, 1990, 36:167–175. This device can be quickly positioned on the patient's head using two ear plugs and a nasal support to locate the device on the skull. However, because these fixation points contact relatively soft tissue, such device inherently lacks the rigidity and reproducibility of bony or dental fixation.

Another prior stereotactic device has also used the upper teeth or alveolar ridge to position the stereotactic device on the patient's skull. The rigid connection between the upper teeth and the skull make the upper teeth a convenient and non-invasive reference point of the skull. This stereotactic device is disclosed in U.K. Patent Publication 2 213 066. Straps or similar structure are used in these devices to secure a mouthpiece of the stereotactic device within the patient's mouth. These straps, however, are awkward and time consuming to use, and can contribute to misalignment in head position. In addition, such straps cannot be easily and immediately removed in exigent circumstances. For instance, in cases where the patient chokes, vomits, or otherwise has trouble breathing, the mouthpiece cannot be quickly removed either by the health care provider or by the patient. In addition, a health care provider also may not immediately recognize the patient's condition because the stereotactic location device has immobilized the patient's head, and the patient may be unable to alert the health care provider of his or her condition.

Another disadvantage of using straps is that they may be variably located in the radiation treatment field, thus compromising the quality and reproducibility of dose delivery, especially where charged particles, such as protons, are used.

As noted above, the diagnostic, planning and treatment stages typically occur over the course of several secessions and involve the use of a variety of different imaging and radiation equipment. In collaborative programs between different institutions, the initial planning procedures typically occur at a facility different from that where the treatment procedures take place. These programs will become increasingly important because only a limited number of hospitals in the United States perform focal radiation therapy.

The orientation of the stereotactic fixation device relative to the reference axes of the scanning planes of the various diagnostic and treatment equipment used throughout the patient's course usually differs. Thus, even though the same fixation apparatus may be attached to the patient's skull during both the diagnostic and treatment stages, the patient's position with respect to the reference axes of the treatment equipment is not exactly replicated as planned.

SUMMARY OF THE INVENTION

In view of the foregoing drawbacks and shortcomings of the prior stereotactic location devices, a need exists for a stereotactic location device which is noninvasive, provides sufficient immobilization, allows accurate re-positioning, is well tolerated by a patient, is quickly released and does not interfere with the medical procedure (e.g., interfere with an external beam in radiotherapy). A need also exists for a way of easily calibrating the orientation of stereotactic location device relative to the reference axes of various diagnostic and treatment equipment at one or more facilities.

In accordance with one aspect of the present invention, a stereotactic fixation apparatus comprises a mouthpiece attached to a stereotactic frame. The mouthpiece has a surface that contacts the patient's hard palate and upper teeth, and also has a port adapted for connection to a source of vacuum. Additionally, the mouthpiece is configured to provide a fluidic path between the surface and the port. In the preferred embodiment, the surface of the mouthpiece is shaped to conform to the hard palate and upper teeth of the patient and has at least one hole that communicates with the port. A normally closed, one-way flow valve may be positioned in the fluidic path between the hole and the port. Additionally, the apparatus preferably includes a vacuum control system which regulates the vacuum and a patient-activated switch for terminating vacuum pressure in the fluidic path.

A further aspect of the present invention relates to a stereotactic fixation apparatus that comprises a platform for supporting the body of a patient. A stereotactic immobilization device, such as a stereotactic frame, contacts the platform at least at one interface region. A port, connected to a source of vacuum, is in fluidic communication with the interface region. When a vacuum pressure is applied to the interface region through the port, the vacuum holds the stereotactic immobilization device against the platform. Preferably, the above-mentioned patient-actuated switch serves to terminate vacuum pressure not only to the mouthpiece, but also to the stereotactic immobilization device.

According to another aspect of the invention, a method of accurately and reproducibly positioning a patient's skull for a medical procedure involves the use of a mouthpiece attached to a stereotactic frame. The mouthpiece is positioned within the patient's mouth so as to extend beneath the patient's hard palate. A vacuum is applied to draw the mouthpiece against the patient's hard palate and upper teeth so as to secure the mouthpiece within the patient's mouth.

Yet another aspect of the invention comprises a method of manufacturing a mouthpiece for a stereotactic fixation apparatus. A dental impression of a patient's teeth is made using a first material, and a study cast of the patient's teeth is made using the dental impression. An impression of the study cast is then made using a second material different from the first material to provide a device that precisely matches the patient's palatal and dental anatomy. A passageway is formed through the mouthpiece to provide a path for drawing the mouthpiece against the interior of the patient's mouth.

An additional aspect of the invention comprises a coupling that couples a stereotactic frame to a mouthpiece. The coupling is configured to provide at least three degrees of rotational movement of the mouthpiece relative to the stereotactic frame and at least two degrees of linear movement of the mouthpiece relative to the stereotactic frame.

In accordance with another aspect of the present invention, a calibration phantom is used to replicate the position of a stereotactic immobilization device relative to a scanning plane of a medical device. The scanning plane has a pair of intersecting axes for reference purposes. The stereotactic immobilization device releasably attaches to at least one point on a support apparatus used with the medical device. The calibration phantom comprises a plurality of markers located in a plane. The markers define at least two intersecting axes. A support is coupled to the markers and is configured to releasably attach to the support apparatus at the same point on the support apparatus that the stereotactic immobilization device is releasably attached.

A further aspect of the invention relates to a stereotactic fixation system which comprises a stereotactic frame. The frame includes an attachment point. A skull immobilization device includes a first adjustable coupling which is adapted to releasably attach to the attachment point of the frame. A calibration phantom also comprises an adjustable coupling and a plurality of markers coupled to the coupling. The markers are located in one plane and defines at least two perpendicular axes. The adjustable coupling is adapted to releasably attach to the attachment point of the frame.

In accordance with a preferred method of calibrating the orientation of reference axes of a scanning plane of a first medical device relative to the position of a detachable fixation device, with the orientation of reference axes of a reference plane of a second medical device relative to the same detachable fixation device, a calibration phantom is provided. The calibration phantom has a plurality of markers that define a pair of perpendicular axes within a plane. The calibration phantom is attached to a first support apparatus used with the first medical device at a location where the detachable fixation apparatus is attached to the first support apparatus. The detachable fixation device is used to immobilize a patient's skull. The markers of the calibration phantom are aligned with the reference axes of the scanning plane such that the axes defined by the markers are parallel with the reference axes of the scanning plane in an aligned position. The calibration phantom then is fixed in this aligned position. After detaching the calibration phantom from the first support apparatus of the first medical device, the calibration phantom later is attached to a second support apparatus used with the second medical device. The calibration phantom is attached to the support apparatus at a location where the detachable fixation apparatus is attached. The second support apparatus is moved to a position where the markers of the calibration phantom align with the reference axes of the second medical device such that the axes defined by the markers coincide with the reference axes of the second medical device. In this manner, the reference axes of the scanning planes of the first and second devices are calibrated.

An additional aspect of the invention comprises a stereotactic fixation system for immobilizing a patient's skull during a medical procedure involving a medical device. The system comprises a platform for supporting a portion of a patient. A stereotactic fixation apparatus contacts the platform at least at one interface region, and a port, which is adapted for connection to a source of vacuum, is positioned in fluidic communication with the interface region between the platform and stereotactic fixation apparatus. The applied vacuum holds the stereotactic fixation apparatus against the platform when vacuum pressure is applied to the interface region through the port. A first sensor is positioned proximate to the interface region, and generates a first input signal which indicates the application or absence of a vacuum at the interface region. The system also includes a patient-activated switch which has at least first and second operational states. The switch generates a second input signal when the switch is in one of the states. A controller receives the first and second input signals from the first sensor and the patient-activated switch, respectively. The controller generates an output signal when the vacuum pressure is applied at the interface region and the patient-activated switch is in the first state. The output signal enables the operation of the medical device.

A preferred method of interlocking the operation of a medical device with the operational state of a quick-release stereotactic fixation apparatus used to immobilize a patient's skull involves sensing the pressure at an interface region between a portion of the stereotactic fixation apparatus and a platform which supports at least the patient's skull. From the sensed pressure, it is determined whether a vacuum is applied at the interface region to hold the stereotactic fixation apparatus against the platform is determined. It also is determined whether a patient-activated switch is in a selected state. When a vacuum is applied at the interface region and the patient-activated switch is in the selected state, a signal which enables the medical device is generated.

BRIEF DESCRIPTION OF THE DRAWINGS

These and other features of the invention will now be described with reference to the drawings of a preferred embodiment which is intended to illustrate and not to limit the invention, and in which:

FIG. 6 is a front elevational view of a mouthpiece/coupling assembly attached to the stereotactic frame of FIG. 1;

FIG. 7 is a side elevational view of the stereotactic frame and mouthpiece/coupling assembly taken along line 7—7 of FIG. 6;

FIG. 8 is a top plan view of the stereotactic frame and mouthpiece/coupling assembly of FIG. 6;

FIG. 9 is an enlarged top perspective view of the mouthpiece/coupling assembly of FIG. 1;

FIG. 10 is a cross-sectional view of the mouthpiece taken along line 10—10 of FIG. 9;

FIG. 14 is a side elevational view of the calibration phantom attached to the stereotactic frame of FIG. 13;

FIG. 15 is a rear elevational view of the calibration phantom and stereotactic frame of FIG. 14 as view in the direction of line 15—15.

DETAILED DESCRIPTION OF A PREFERRED EMBODIMENT

Figure 1:
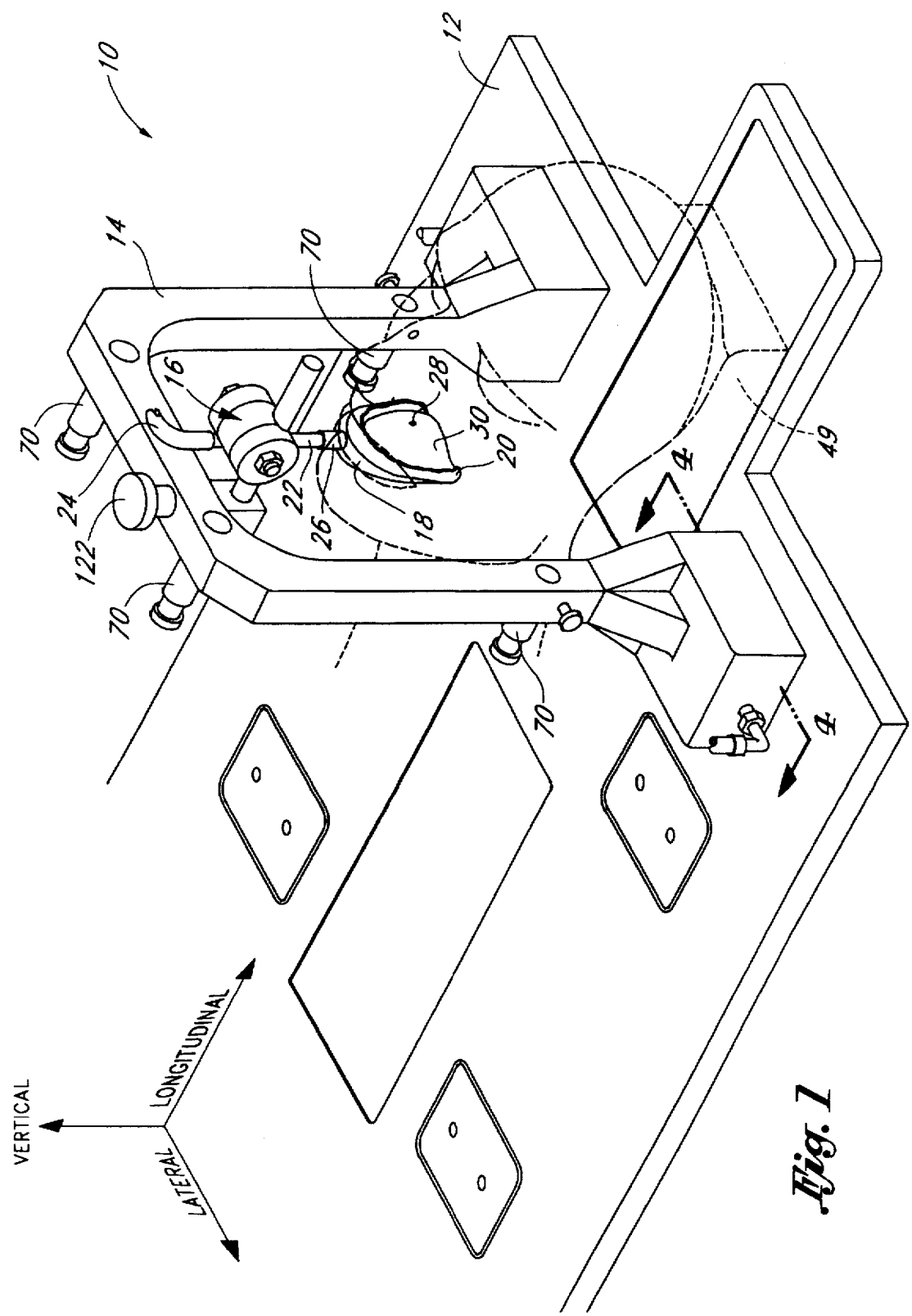
FIG. 1 is a top perspective view a vacuum-assisted stereotactic fixation apparatus in accordance with one preferred embodiment of the present invention.

FIG. 1 illustrates a stereotactic fixation apparatus 10 configured in accordance with a preferred embodiment of the present invention. The stereotactic fixation apparatus 10 is designed to immobilize a patient's skull, and is typically used with focal radiation therapy involving proton beam treatment. It is contemplated, however, that the present stereotactic fixation apparatus can be used in connection with a variety of medical diagnostic and treatment procedures.

With reference to FIG. 1, the stereotactic fixation apparatus 10 principally comprises a generally flat adaptor board or platform 12 supporting a stereotactic frame 14. A vacuum interface is used to secure the frame 14 to the adaptor board 12, as discussed in detail below.

A coupling or universal joint 16 extends outwardly from the frame 14 and supports a mouthpiece 18. The universal joint 16, which connects the mouthpiece 18 to the frame 14, allows a wide range of different positions and orientations of the mouthpiece 18 in relation to the stereotactic frame 14. Once set in a desired position, the universal joint 16 is locked and remains attached to the mouthpiece 18 throughout all subsequent planning and treatment phases of the patient's course. In this manner, the universal joint 16 forms a mechanical memory of the patient's skull position with respect to the stereotactic frame 14.

The mouthpiece 18 includes an acrylic impression (i.e., a bite block 20 formed as an impression) of the patient's upper mouth. A vacuum is used to removably secure the mouthpiece 18 onto the hard palate and upper teeth of the patient. For this purpose, the mouthpiece 18 connects to a vacuum source via a rigid tube 22, which passes through the universal joint 16 and connects to a flexible vacuum line 24. The mouthpiece 18 is also configured to provide a fluidic path between a port 26 to which the tube is connected and at least one hole 28 in an upper surface 30 of the acrylic impression 20. When used, a vacuum is applied between the mouthpiece 18 and the patient's upper mouth to precisely position and secure the acrylic impression 20 to the patient's dentition and hard palate.

Figure 2:
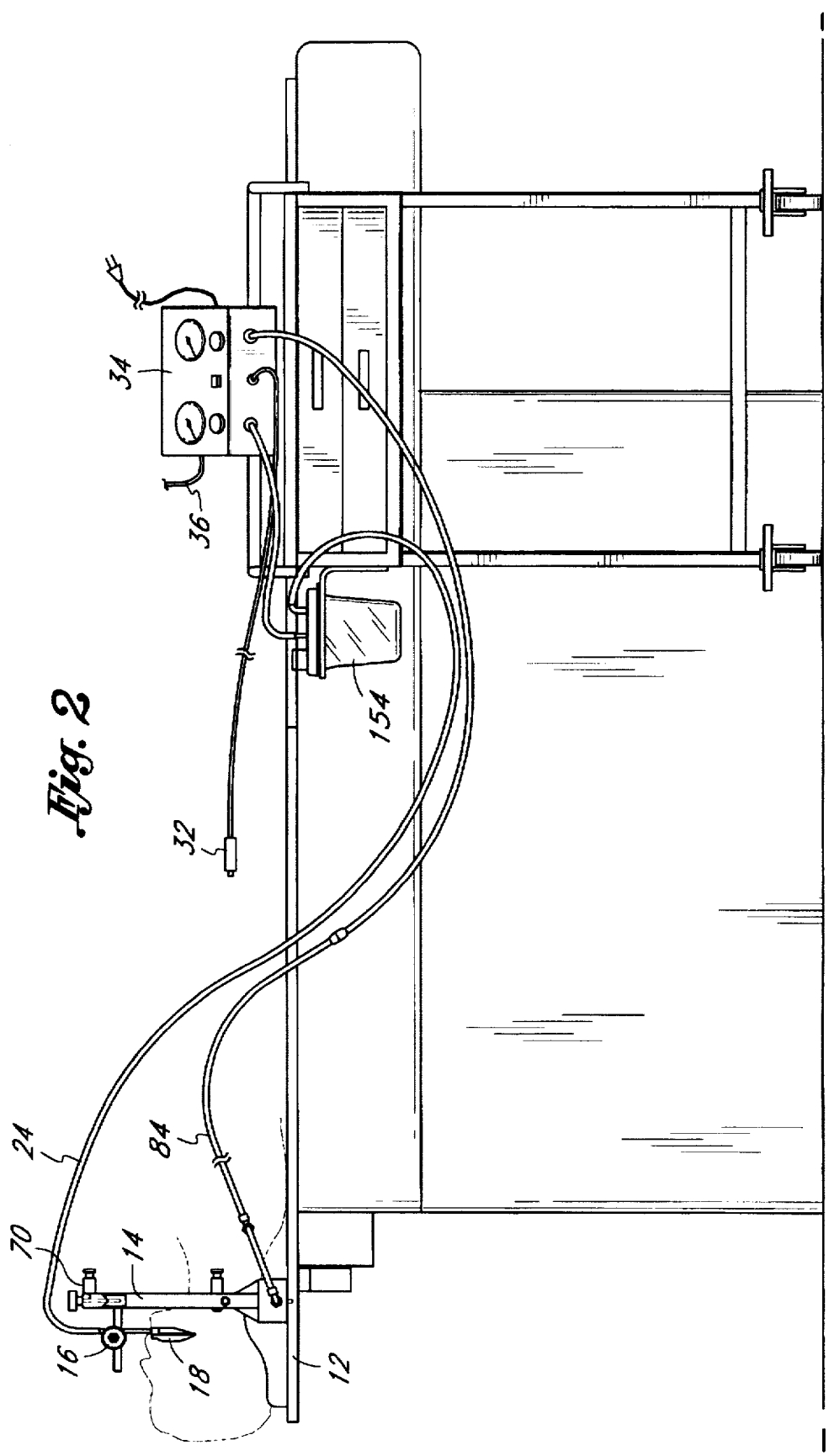
FIG. 2 is a schematic front elevational view of the stereotactic fixation apparatus of FIG. 1.

With reference to FIG. 2, the stereotactic fixation apparatus 10 may also include a patient-activated quick-release mechanism with a safety interlock. This quick-release mechanism includes a patient-activated switch 32 connected to a vacuum control system 34. The vacuum control system 34 controls the application of vacuum pressure to the mouthpiece 18 and to the vacuum interface between the stereotactic frame 14 and the adaptor board 12, as discussed in detail below. When the patient activates the switch 32, the vacuum control system 34 disconnects the vacuum sources from the mouthpiece 18 and the adaptor board 12/stereotactic frame 14 interface so that the patient can dislodge the mouthpiece 18 from his or her mouth, as well as remove the frame 14 from a position surrounding the patient's head.

The vacuum control system 34 also electronically communicates via line 36 with a medical diagnostic or treatment device (not shown in FIG. 2), such as, for example, a CAT (computer axial tomography) or MRI (magnetic resonance image) scanner, or an irradiation treatment device. When the patient activates the switch 32, the control system 34 deactivates the medical diagnostic or treatment apparatus so as not to expose non-target site tissue to any irradiation emitted by the diagnostic or treatment apparatus and to prevent misalignment of the patient's head during diagnostic or treatment procedures which may lead to unwanted exposure of non-target site tissue to irradiation.

For purposes of describing the preferred embodiment, a coordinate system is provided as illustrated in FIG. 1.

Additionally, as used herein, "the longitudinal direction" refers to a direction substantially parallel to the longitudinal axis. "The lateral direction" and "the vertical direction" are likewise in reference to the lateral axis and vertical axis, respectively.

The individual components of the stereotactic fixation apparatus 10 will now be described in detail with reference to FIGS. 1–10.

Adaptor Board

Figure 3:
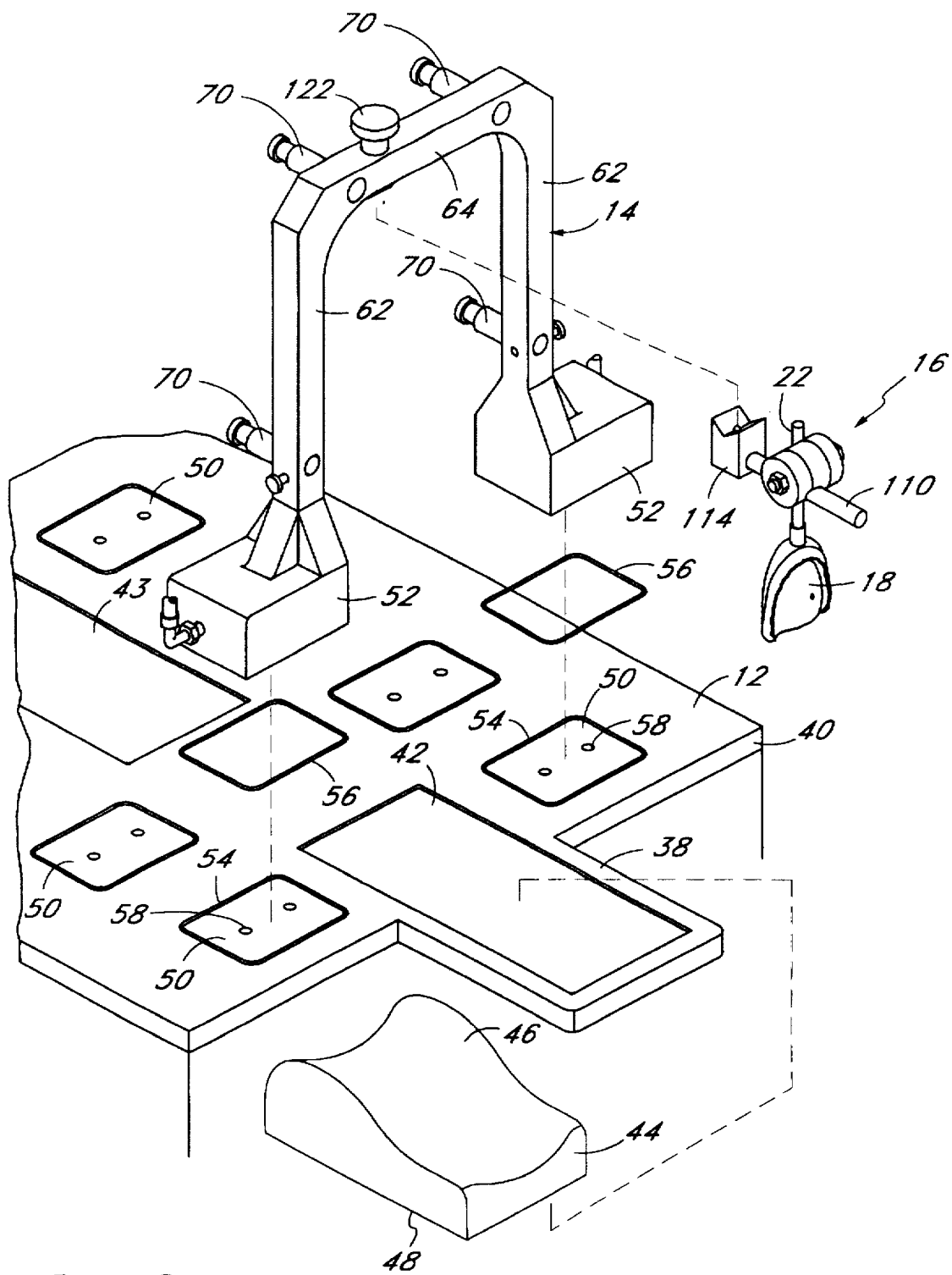
FIG. 3 is an exploded top perspective view of the stereotactic fixation apparatus of FIG. 1.

FIGS. 1–3 best illustrate the adaptor board 12. The adaptor board 12 generally has a rectangular shape sized to support an adult body in a supine position. The adaptor board 12 desirably has a size and shape which is coextensive with conventional gurneys or hospital diagnostic and treatment tables. The adaptor board 12 can thus be placed onto of a diagnostic or treatment table or gurney when a medical procedure is preformed using the present stereotactic fixation apparatus 10. It is also contemplated that the adaptor board 12 can alternatively be integrally formed with a dedicated diagnostic or radiation therapy treatment table or gurney.

As illustrated in FIG. 3, the adaptor board 12 may include a rectangular-shaped plank 38 which cantilevers from a superior end 40 of the adaptor board 12. The plank 38 has a width and a length slightly larger than that of a human skull. In an exemplary embodiment, the plank 38 has a length approximately equal to 10 inches (25.4 cm) and a width approximately equal to 8 inches (20.3 cm). It is understood, however, that the plank 38 could have a variety of shapes and sizes, depending upon the specific application of the stereotactic fixation apparatus 10.

The adaptor board 12, proximate to its superior end 40, defines a first rectangular recess 42 positioned generally symmetric with a longitudinal axis of the adaptor board 12. The recess 42 has a length that extends from a point proximate to the superior end 40 into the plank 38. The recess 42 is sized to receive a portion of a headrest 44 (see FIG. 3), which supports the patient's head and neck during the medical procedure.

The adaptor board 12 additionally includes a second rectangular recess 43 also positioned generally symmetrically with the longitudinal axis of the adaptor board 12. The second recess 43 is located below the first recess 42, and has a shape and size substantially identical to those of the first recess 43.

As illustrated in FIG. 3, the headrest 44 used with the adaptor board or platform 12 has an arcuate upper surface 46 which cradles the patient's skull and the nape of the patient's neck. A base 48 of the headrest 44 has a rectangular shape of a width and length generally equal to those of the recesses 42, 43 so as to be snugly received by recesses 42, 43.

The headrest 44 may be formed of any of a wide-variety of material of sufficient rigidity and integrity to support the patient's head and neck. In an exemplary embodiment, the headrest 44 is vacuum-formed plastic. However, those skilled in the art will realize that the headrest 44 can be formed of a variety of different materials by a variety of different methods, known or developed in the art.

With reference to FIG. 3, the adaptor board 12 defines a series of paired stations 50 which interface with corresponding footings 52 of the stereotactic frame 14. Each station 50 includes a generally rectangularly shaped groove 54 into which a correspondingly shaped O-ring 56 is seated. The O-ring 56 is advantageously positioned on the adaptor board 12 rather than on the corresponding footing 52 because the O-ring 56 is less likely to fall off or be displaced when positioned on the adaptor board 12. However, it is contemplated that the O-ring could be secured to the frame footing 52.

The O-ring 56 desirably has a diameter larger than the depth of the corresponding groove 54. The O-ring 56 thus extends above the surface of the adaptor board 12 when seated within the groove 54.

The shape and size of each O-ring 56 desirably matches the general shape and size of the stereotactic frame footing 52. More preferably, each O-ring 56 has a corresponding shape that is slightly smaller than the periphery of the footing 52 such that with the footing 52 positioned over the O-ring 56, the entire O-ring 56 is compressed between the adaptor board 12 and the bottom surface of the footing 52.

Figure 4:
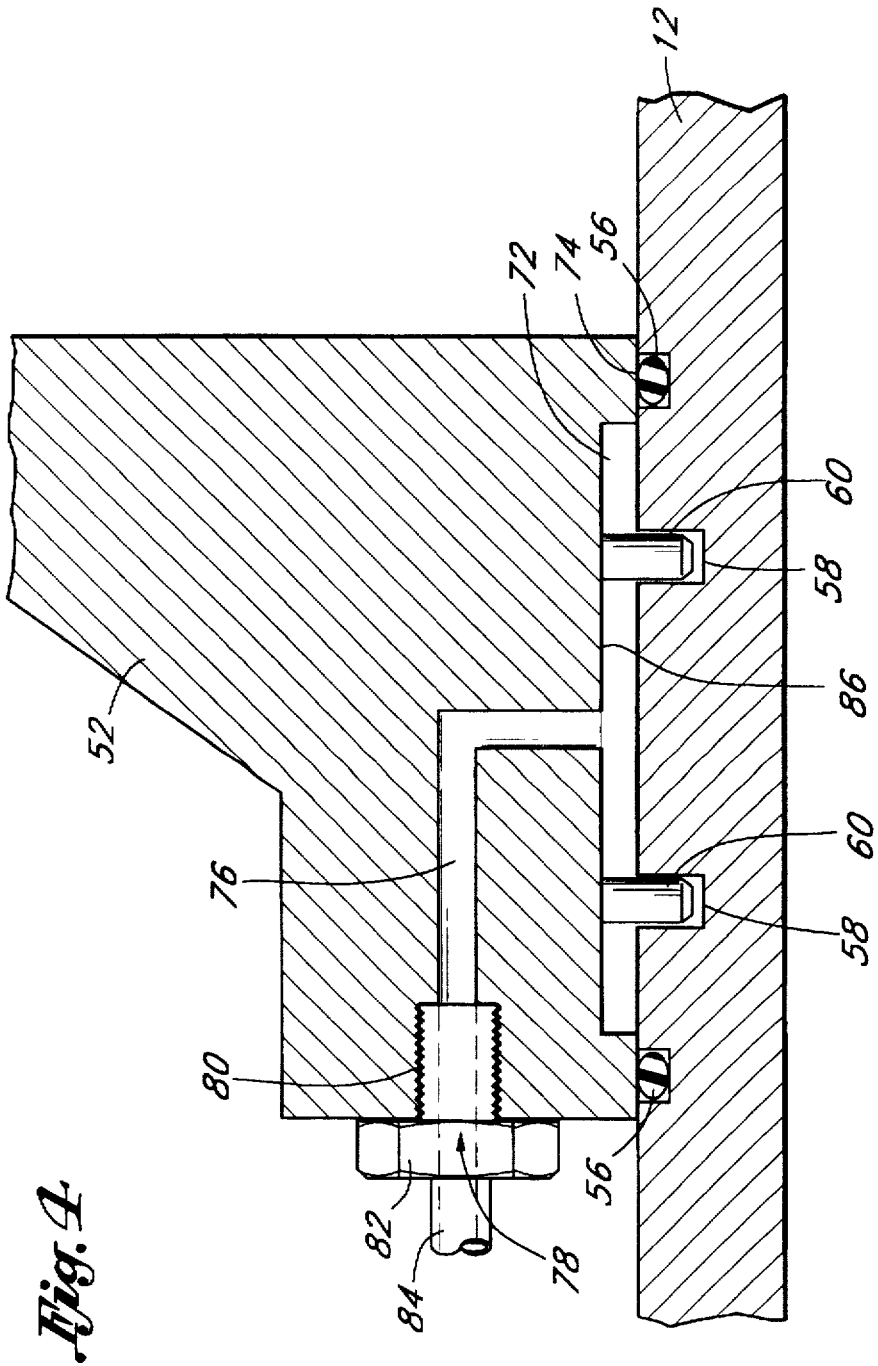
FIG. 4 is a cross-sectional view of a footing of a stereotactic frame taken along line 4—4 of FIG. 1.

With reference to FIG. 4, each station 50 also includes at least two holes 58 sized and positioned to receive guide pins 60 of the corresponding footing 52. These holes 58 are positioned with respect to the O-ring 56 such that with the guide pins 58 inserted into the holes 58, the footing 52 completely covers the O-ring 56. The O-ring 56 thus seals the periphery of the footing 52 at the interface between the footing 52 and the adaptor board 12.

Figure 5C:
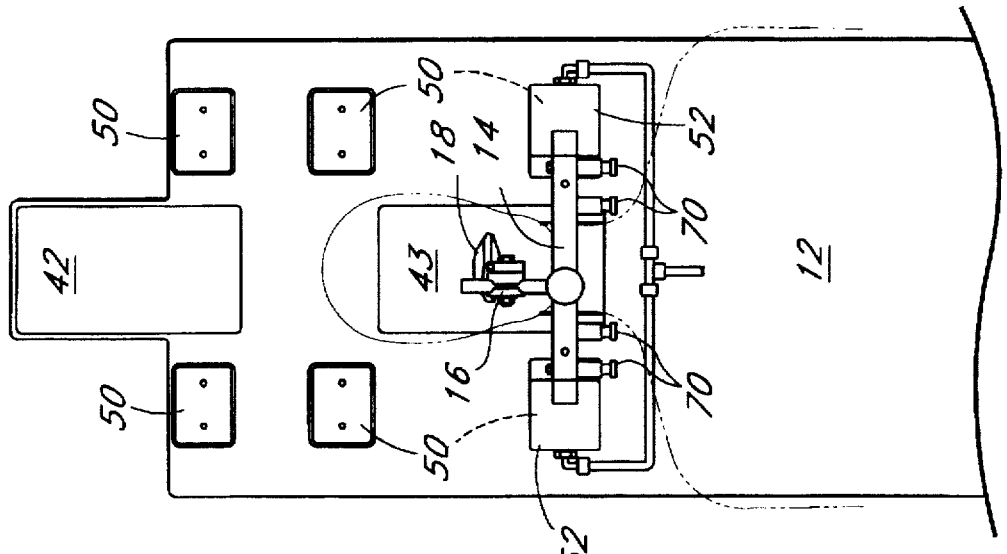
FIG. 5c is a schematic top plan view of the stereotactic fixation apparatus of FIG. 1 with the stereotactic frame in a third treatment position.
Figure 5B:
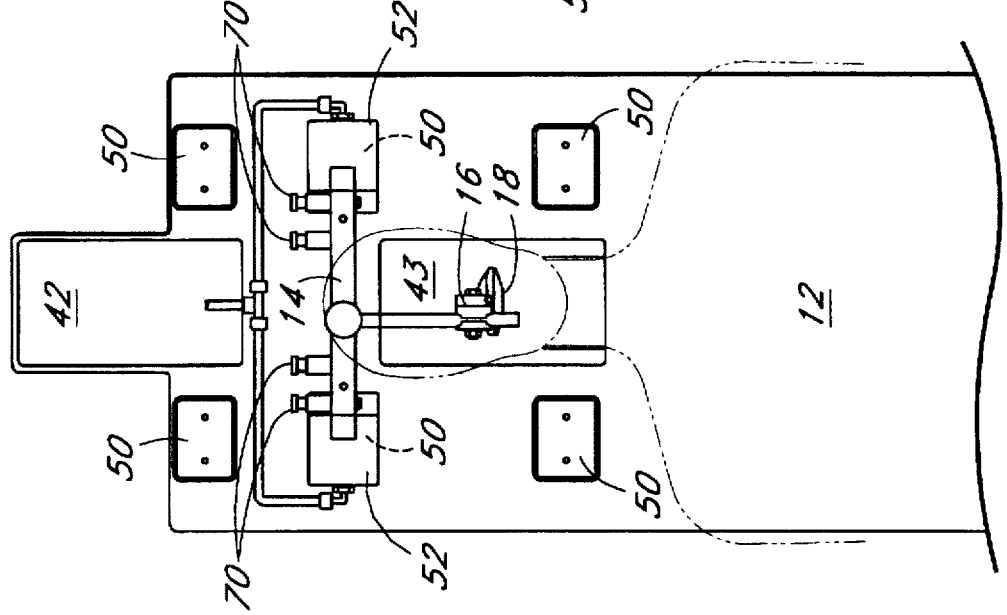
FIG. 5b is a schematic top plan view of the stereotactic fixation apparatus of FIG. 1 with the stereotactic frame in a second treatment position.
Figure 5A:
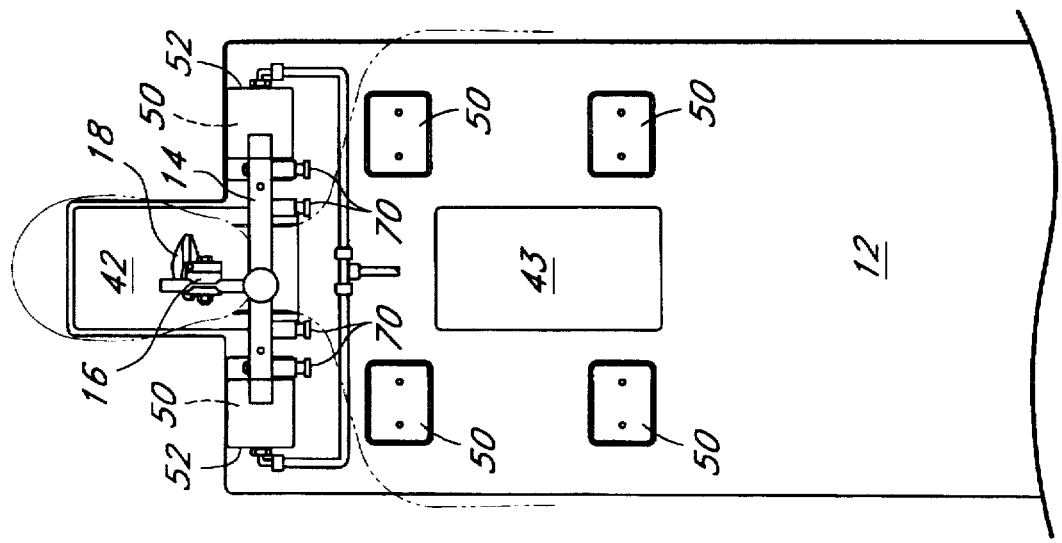
FIG. 5a is a schematic top plan view of the stereotactic fixation apparatus of FIG. 1 with the stereotactic frame in a first treatment position.

FIGS. 5a–5c illustrate the plurality of paired stations 50 of the adaptor table 12. The spacing between these stations 50 is set to position the stereotactic frame 14 either proximate to the patient's shoulders or proximate to the superior portion of the patient's head. The variety of positions of the stereotactic frame 14 on the adaptor board 12 permits the present stereotactic fixation apparatus 10 to be used in radiotherapy procedures where the target is located above the base of the skull or in those procedures where the target is located below the base of the skull.

Stereotactic Frame

With reference to FIG. 3, the stereotactic frame 14 generally has an inverted "U" shape formed by two vertical legs 62 interconnected by an upper horizontal leg 64. The stereotactic frame 14 desirably has a sufficient lateral width and vertical height to surround the skull of the patient.

Each vertical leg 62 terminates in a footing 52. As discussed above, the footings 52 rest flush against the top surface of the adaptor board 12.

As best seen in FIGS. 6 and 7, the horizontal leg 64 of the stereotactic frame 14 includes a tang 66 to which the universal joint 16 is attached. The tang 66 extends from the horizontal leg 64 toward the adaptor base 12, and, as best seen in FIG. 7, has a "V" shape. With reference to FIG. 6, the tang 66 extends from the horizontal leg 64 at an asymmetric position with respect to the vertical legs 62. This asymmetric position is selected to symmetrically position the mouthpiece 18 between the vertical legs 62 when the coupling 16 is attached to the tang 68, as best seen in FIG. 6.

The horizontal leg 64 also includes a bore 68 that extends in the vertical direction through the horizontal leg 64. An axis of the bore 68 is desirably aligned with the center line of the V-shaped tang 70.

The stereotactic frame 14 also includes a plurality of pins 70 positioned on the vertical and horizontal legs 62, 64. The pins 70 are used to support a stereotactic reference phantom (not shown), which is used to align the stereotactic target with the isocenter of the treatment machine, as discussed more fully in the article "Research in Immobilization and Repeatable Positioning," *Proton Treatment Center Newsletter*, vol. 2, no. 4, Oct. 1992, which is incorporated by reference herein.

With reference to FIG. 4, each footing 52 has a generally rectangular block shape. A recess 72 extends into the footing 52 from a bottom surface 74. The footing 52 also includes a channel 76 that extends from the recess 72 to an effluent port 78, desirably positioned on the outer lateral side of the footing 52. It should be noted, however, that a recess, channel and port could alternatively be formed in the adaptor board 12.

The effluent port 78 is formed by a threaded counterbore 80, which circumscribes the channel 76. A conventional tube fitting 82 is threaded into the threaded bore 80 to complete the port 78.

A vacuum tube 84 is attached to the fitting 82 to interconnect the vacuum tube 84 to the footing 52 and to place the recess 72 in fluidic communication with the vacuum tube 84.

As noted above, each footing 52 includes at least two guide pins 60 that extend downwardly from a bottom surface 86 of the recess 82. The guide pins 60 are advantageously positioned in reference to the periphery of the recess 72 so as to position the recess 72 within the circumference of the O-ring 56 when the guide pins 60 are inserted into the corresponding holes 58 in the adaptor board 12.

Universal Joint

With reference to FIG. 9, the universal joint 16 is desirably formed by a plurality of adjacent discs. In an exemplary embodiment the universal joint 16 includes three adjacent discs 88, 90, 92. The axes of the discs 88, 90, 92 are collinear. A bore 94, concentrically positioned about the axis of the disc 88, 90, 92, extends through the disc assembly.

A fastener 96, such as a nut 98 and bolt 100, is used to join the discs 88, 90, 92 together. The bolt 98 passes through the bore 94. The nut 96 threads onto the bolt 98 from the opposite side to secure the bolt 98 within the bore 94.

The first end disc 88 includes a first bore 102 that passes through the first end disc 88 in a direction generally normal to the axis of the central bore 94. The first bore 102 is also offset from the center of the disc 88 so as not to intersect with the central bore 94. Thus, the first bore 102 extends along an arc length of the first end disc 88, rather than along a diameter of the first end disc 88. So positioned, a small arc length of the first bore 102 is truncated. That is, the first bore 102 breaks through a lateral side surface (not shown) of the disc 88. The corresponding truncated arc length is desirably less than 30°, and more preferably equal to about 10°.

The first bore 102 receives the generally rigid tube 22, which in turn is attached to the mouthpiece 18 via the tube fitting 26 positioned on an anterior end 108 of the mouthpiece 18. The tube 22 has a diameter slightly smaller than that of the first bore 102 so that the tube can be rotated within the bore 102.

With the tube 22 inserted through the first bore 102, a small portion of the tube's external surface extends beyond the flat lateral side surface of the first end disc 88 and lightly contacts the opposing flat lateral surface of the center disc 90. When the fastener 96 is loosened, the tube 22 can rotate relative to the first end disc 88, and the first end disc 88 can rotate relative to the center disc 90. When the fastener 96 is tightened, however, the frictional contact between the first end disc 88 and the center disc 90 prevents the first end disc 88 from rotating relative to the center disc 90. Likewise, the frictional contact between the center disc 90 and the exterior portion of the tube 22 that extends beyond the lateral side surface of the first end disc 88 prevents the tube 22 from rotating within the first bore 102 of the first end disc 88.

The universal joint 16 also includes a mounting rod 110 that extends in the longitudinal direction, normal to the common axis of the disc assembly. The rod 110 extends through a second bore 112. The second bore passes through the central disc 90 and a second end disc 92 at the interface of the central disc 90 and the second end disc 92. The second bore 112 is also offset from the center of the discs 90, 92 so as not to intersect with the central bore 94. Thus, the second bore 112 extends along an arc length of the discs 90, 92, rather than along a diameter of the discs 90, 92.

The rod 110 is inserted through the second bore 112 and is captured between the center disc 90 and the second end disc 92. This configuration allows the universal joint 16 to be rotated about the rod 110 when the fastener 96 is loosened. When the fastener 96 is tightened, the central disc 90 and the second end disc 92 clamp against the rod 110 to prevent rotation of the disc assembly about the rod 110.

With reference to FIG. 9, one end of the support rod 110 connects to a mount block 114. The mount block 114 has a generally rectangular block-like shape with a V-shaped notch 116 formed on an upper end. The shape of the V-notch 116 desirably matches that of the V-shaped tang 66 on the stereotactic frame 14. The mount block 114 also includes a threaded bore 118 that extends in the vertical direction through the block 114. The axis of the bore 118 substantially coincides with a center line of the block 114 in the vertical direction.

As discussed below, the mounting block 114 is attached to the horizontal leg 64 of the stereotactic frame 14, and is positioned thereon by inserting the V-shaped tang 66 into the correspondingly V-shaped notch 116 of the mount block 114. With reference to FIG. 7, an elongated threaded shaft 120 of the knob 122 is inserted through the bore 68 and engages the threaded bore 118 of the mount block 114. In this manner, the universal joint 16 is secured to the stereotactic frame 14.

Mouthpiece

With reference to FIGS. 9 and 10, the mouthpiece 18, includes the acrylic impression 20 attached to an impression tray 124. The mouthpiece 18 generally has a U-shape that corresponds to the shape of the patient's upper dentition.

FIG. 10 illustrates a cross section of the mouthpiece 18. The acrylic impression 20 has an upper surface 30 that is, as noted above, a reproduction of an impression of the patient's dentition and hard palate. The acrylic impression 20 includes a skirt 128, which extends upwardly and surrounds the circumference of the U-shaped acrylic impression 20 so as to extend over the outer surfaces of the patient's upper teeth and the poster border of the hard palate when inserted in the patient's mouth.

A hollow 130 is formed inside the acrylic impression 20. The aperture 28 is formed between the inner surface of the hollow 130 and the upper surface 30 of the acrylic impression 20. The aperture 28 places the hollow 130 in fluidic communication with the upper surface 30 of the acrylic impression 20. A flat bottom surface 132 circumscribes the hollow 130, as well as extends around the periphery of the acrylic impression 20.

The acrylic impression 20 is formed by first taking an impression of the patient's dentition and upper palate. A putty-like material, such as, for example, algenate or silicon, is spread into a conventional dental tray. The dental tray is then placed in the patient's mouth and is pushed upwardly against the upper teeth and hard palate to take an impression. The material desirably hardens within a short period of time (e.g., 90 seconds). The hardened impression is then removed from the patient's mouth.

A study cast is made of the patient's dentition and hard palate using the dental impression. A study cast, as known in the art, is a permanent, exact reproduction of the patient's upper dentition and roof of mouth.

The cast, in turn, becomes the basis for the acrylic impression itself. The acrylic impression 20 is formed by sputtering a layer of self-curing orthodontic resin over the study cast. This process is repeated several times until the acrylic impression 20 has a desired thickness. The acrylic impression 20 advantageously has a sufficient thickness to provide the necessary structural integrity such that the acrylic impression 20 does not crack or break during use. In an exemplary embodiment, the acrylic impression 20 has a thickness equal to about ⅛ inch (0.3 cm). It is contemplated, however, that the acrylic impression 20 can have a thickness of any of a variety of sizes depending upon the particular application of the acrylic impression 20. The acrylic impression 20 is then attached to the impression tray 124 using a moldable orthodontic resin, such as TRIAD®-VLC resin, which is cured with visible light.

With the acrylic impression 20 attached to the study cast, the sealing skirt 128 is put around the circumference of the acrylic impression 20 and molded to the outer surface of the upper teeth and the poster circumference of the hard palate. A silicon-based impression material, such as, for example, Extride®-Kerr Polyvinylsiloxane, is preferably used to form the seal 120.

Formed from the study cast, the acrylic impression 20 reproduces the impression, not only of the patient's teeth (or alveolar ridge, if the patient is edentulous) but also the entire surface of the hard palate.

The hole 28 is then placed in the upper surface 30 of the acrylic impression 20 to form a passageway from the upper surface 30 into the hollow 130 inside the acrylic impression 20.

A normally closed, one-directional flow valve 131 may be used with the acrylic impression 20 as an added safeguard to prevent the patent from dislodging the mouthpiece 18. With reference to FIG. 10, the valve 131 includes a valve body 133 with a central channel 135 passing therethrough. The channel 135 of the valve 131 desirably has a diameter matching that of the hole 28 in the acrylic impression upper surface 30.

The valve 131 further includes a valve membrane 141 formed of an elastic material with sufficient structural integrity to normally close the channel 135 of the valve 131, yet open slightly when the pressure in the hollow 130 of the acrylic impression 20 is less than the pressure in the channel 135. The elastic material preferably comprises a silicon sheet; however, it is understood that any of a wide variety of materials may be used as well. The valve membrane 141 is fixed to the valve body 133 at two points located on opposite sides of the channel 135.

A second end 143 of the valve is attached to the inner surface of the hollow 130 of the acrylic impression 20 by an epoxy adhesive. Desirably, the hole 28 in the upper surface 30 of the acrylic impression 20 and the channel 135 of the valve 131 are aligned.

The volume within the valve body 133 desirably is substantially less (e.g., 10% or less) than the volume within the hollow 130 of the acrylic impression 20.

As illustrated in FIG. 10, the impression tray 124 includes a generally flat platform 134 having a size and shape generally coextensive with that of the acrylic impression bottom surface 132. The platform 134 includes a recess 136 positioned within the circumferential edges of the platform 134.

As best seen in FIG. 7, the impression tray 124 desirably has a minimal profile to minimize the invasiveness of the impression tray 124 when inserted in the patient's mouth. In the exemplary embodiment, the maximum thickness of the impression tray 124 is about 0.5 inch (1.3 cm); however, those skilled in the art will readily appreciate that the impression tray 124 could be formed of a wide variety of sizes, depending upon the specific application of the mouthpiece 18. In an exemplary embodiment, as illustrated in FIG. 10, the impression tray 124 has a generally triangular cross-sectional shape. This shape reduces the obtrusiveness of the mouthpiece 18 when worn by the patient, as the width of the mouthpiece 18 is reduced towards the back of the patient's palate so as to fit more comfortably within the patient's mouth.

FIG. 10 illustrates an internal channel 138 formed between the anterior end 108 of the impression tray 124 and the platform recess 136. The channel 138 preferably has a circular cross-sectional shape equal to that of the inner lumen of the tube 22. The channel 138 extends normal to both the platform surface 134 and to the anterior end 108 of the impression tray 124 and includes a 90° bend between these two sections of the channel 138. The wall of the channel 138 may include a chamfer 140 at the 90° bend to improve fluidic flow through the channel 138, as known in the art.

The anterior end 108 of the impression tray 124 also includes a counterbore 142 that circumscribes the channel 138. The counterbore 142, as illustrated in FIG. 10, receives the conventional tube fitting 26 to attach the tube 22 to the impression tray 124, with the inner lumen of the tube 22 communicating with the channel 138 of the impression tray 124. The fitting 26 desirably has a diameter substantially equal to or less than the width of the impression tray 124 at its anterior end 108 such that the fitting 26 sits flush against the anterior end 108 of the impression tray 124.

When the acrylic impression 20 is mounted to the tray 124, a fluidic path is formed from the port 26 of the tray 124, through the channel 138, into the hollow 130 of the acrylic impression 20, and through the hole 28 in the upper surface 30 of the acrylic impression 20.

Patient-Activated Quick-Release Mechanism

As discussed above, the stereotactic fixation apparatus 10 may also include a patient-activated quick-release mechanism. With reference to FIG. 2, the patient-activated switch 32 communicates with the vacuum control system 34. The vacuum control system 34 controls the application of vacuum pressure to the mouthpiece 18 and to the interface region between the stereotactic frame 14 and adaptor board 12. In an exemplary embodiment, the vacuum control system includes at least two solenoid valves (not shown) which are positioned between the vacuum source and the ports 78, 26 of the stereotactic frame footings 52 and the mouthpiece 18, respectively. When the stereotactic frame 14 is attached to a patient's skull, the vacuum control system 34 holds the solenoid valves open such that a vacuum is drawn in the mouthpiece 18 and at the interface between the stereotactic frame 14 and the adaptor board 12. In this manner, the mouthpiece 18 is drawn against the patient's hard palate, and the vacuum created between the footings 52 of the stereotactic frame 14 and the adaptor board 12 holds the stereotactic frame 14 against the adaptor board 12.

If the patient activates the switch 32, the vacuum control system 34 closes the solenoid valves to disconnect the vacuum source from the footings 52 of the stereotactic frame 14 and from the mouthpiece 18. The patient may then dislodge the mouthpiece 18 from his or her mouth and remove the frame 14 from the position surrounding the patient's head. In this manner, the patient can quickly remove the stereotactic frame and mouthpiece if the patient chokes, vomits, or otherwise experiences trouble breathing.

Figure 11:
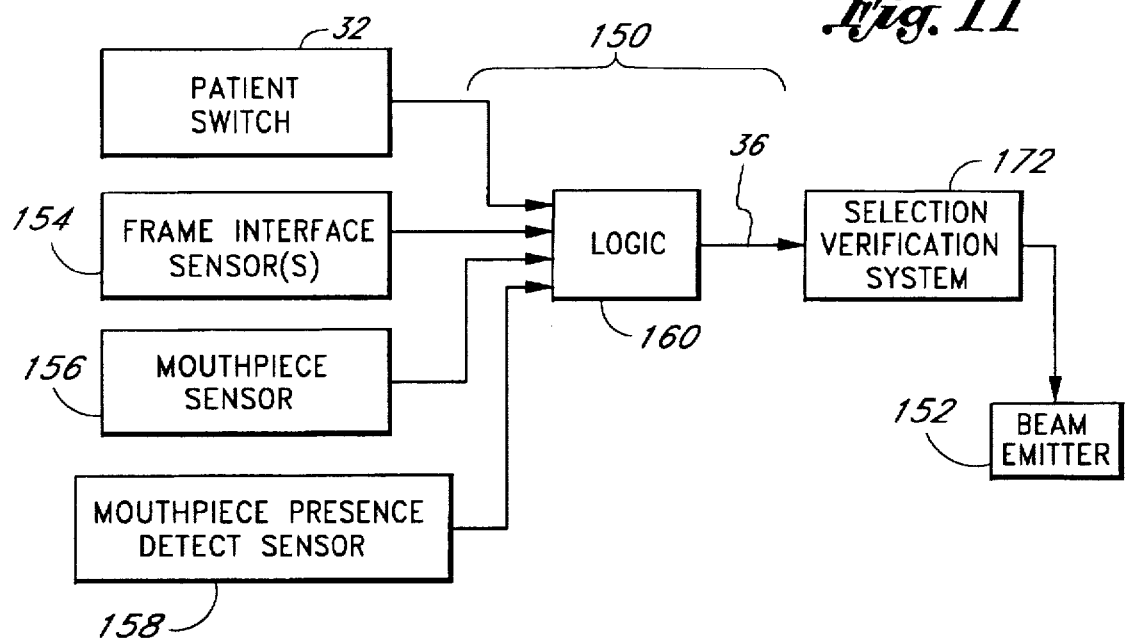
FIG. 11 is a schematic block diagram of an interlock system used with the stereotactic fixation apparatus of the present invention.

As discussed above, the vacuum control system 34 also can communicate with the medical diagnostic or treatment device (not shown) used in conjunction with the stereotactic fixation apparatus 10. FIG. 11 schematically represents an interlock subsystem 150 of the control system 34 which enables and disables the medical treatment device 152 (e.g., a proton beam emitter).

As seen in FIG. 11, the interlock system 150 includes several sensors 154, 156, such as, for example, vacuum switches, located at the frame/platform interface regions 72, and in or proximate to the mouthpiece 18, respectively. The sensors 154, 156 detect the application of a vacuum and generate a signal which indicates the presence or absence of a vacuum at the corresponding location. The interlock system 150 also may include a presence detect sensor 158, e.g., a micro-switch(es), which the stereotactic frame 14 activates when positioned over one of the pairings of stations 50 on the platform 12.

The interlock system 100 also includes logic 160 which selectively generates an enable signal depending upon the presence or absence of vacuum at the mouthpiece 18 and at the frame/platform interface region 72, and depending upon whether the patient has actuated the hand held safety switch 32. For this purpose, the logic 160 receives input signals from the frame interface vacuum sensors 154, the mouthpiece vacuum sensor 156, the presence detect sensor 158, and the patient switch 32, and interprets the signals to determine whether to generate an enable signal. The logic 160 may include hard wired logic circuitry, including comparators and/or relays, or a microprocessor based platform, including memory, programmed to execute the desired function.

Figure 12:
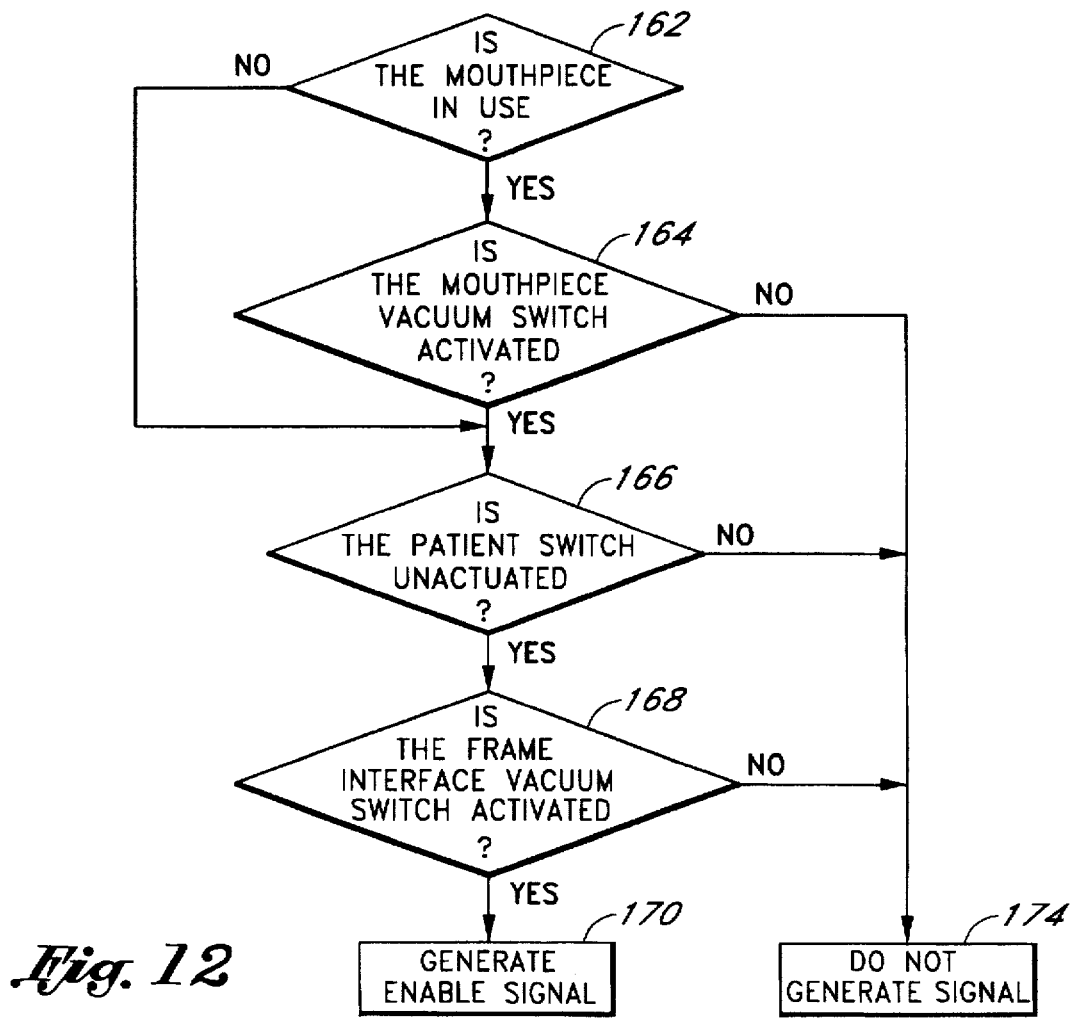
FIG. 12 is a flow chart which illustrates the general function of the interlock system.

FIG. 12 is a flow chart illustrating the general function performed by the logic 160. It should be understood that the function can be performed in any of a variety of sequences.

As represented in decision block 162, the logic 160 determines whether the mouthpiece 18 is in use or whether another fixation apparatus is being used with the system (such as, for example, the immobilization mask described below). In the illustrated embodiment, the logic 160 determines whether the input signal for the micro-switch 158 indicates that the footings of the stereotactic frame 52 have been positioned over the corresponding stations 50 of the platform 12.

If the mouthpiece and corresponding stereotactic frame 14 are in use, the logic 160 determines whether the vacuum switch 156 on the mouthpiece 18 is activated, which indicates the presences of a vacuum, as discussed above. Decision block 164 of FIG. 12 represents this function. For this purpose, the logic 160 examines the signal from the vacuum switch 158.

If the mouthpiece 18 is not in use (decision block 162), the logic 160 skips the determination of whether the mouthpiece vacuum switch 158 is activated (i.e., skips decision block 164).

As represented in decision block 166, the logic 160 also determines whether the patient's hand held switch 32 is unactuated by examining the corresponding input signal. If unactuated, the logic 160 proceeds with its function.

The logic further determines whether the vacuum switch 154 at the platform/frame interface region 72 is activated, which indicates the presences of a vacuum, as discussed above. Discussion block 168 represents this function. For this purpose, the logic 160 examines the input signal from the corresponding vacuum switch(es) 154.

If all of the vacuum switches 154, 156 are actuated and the patient's emergency switch 32 remains unactuated, the logic 160 generates an enable signal, as represented in operation block 170.

As schematically illustrated in FIG. 11, a selection verification system 172 receives the enable signal from the logic 160 of the interlock system 100 via the transmission line 36. If the treatment device 152 (i.e., beam emitter) is otherwise configured correctly, as determined by the selection verification system 172, and a treatment beam has been requested, the selection verification system 172 activates treatment device 152. A suitable selection verification system 172 is disclosed in U.S. Pat. No. 5,260,581, issued Nov. 9, 1993, which is hereby incorporated by reference.

If, however, any one of the vacuum switches 154, 156 is not activated (see decision blocks 164, 168 of FIG. 12), or if the patient switch 32 is activated (see decision block 166), the logic 160 does not generate an enable signal, as represented in operation block 174. The selection verification system 172 (FIG. 11) advantageously cannot operate the treatment device 152 without receiving an enable signal from the interlock system 100.

Thus, for instance, when the patient activates the safety switch 32, the control system 34 interrupts the enable signal to disable the medical device 152. Any radiation emitted by the medical device 152 immediately ceases so as not to expose non-targeted tissue to irradiation. Thus, the patient can dislodge and remove the restraints of the mouthpiece 18 and stereotactic frame 14 without the danger of unintentional irradiation.

Calibration Phantom

Figure 13:
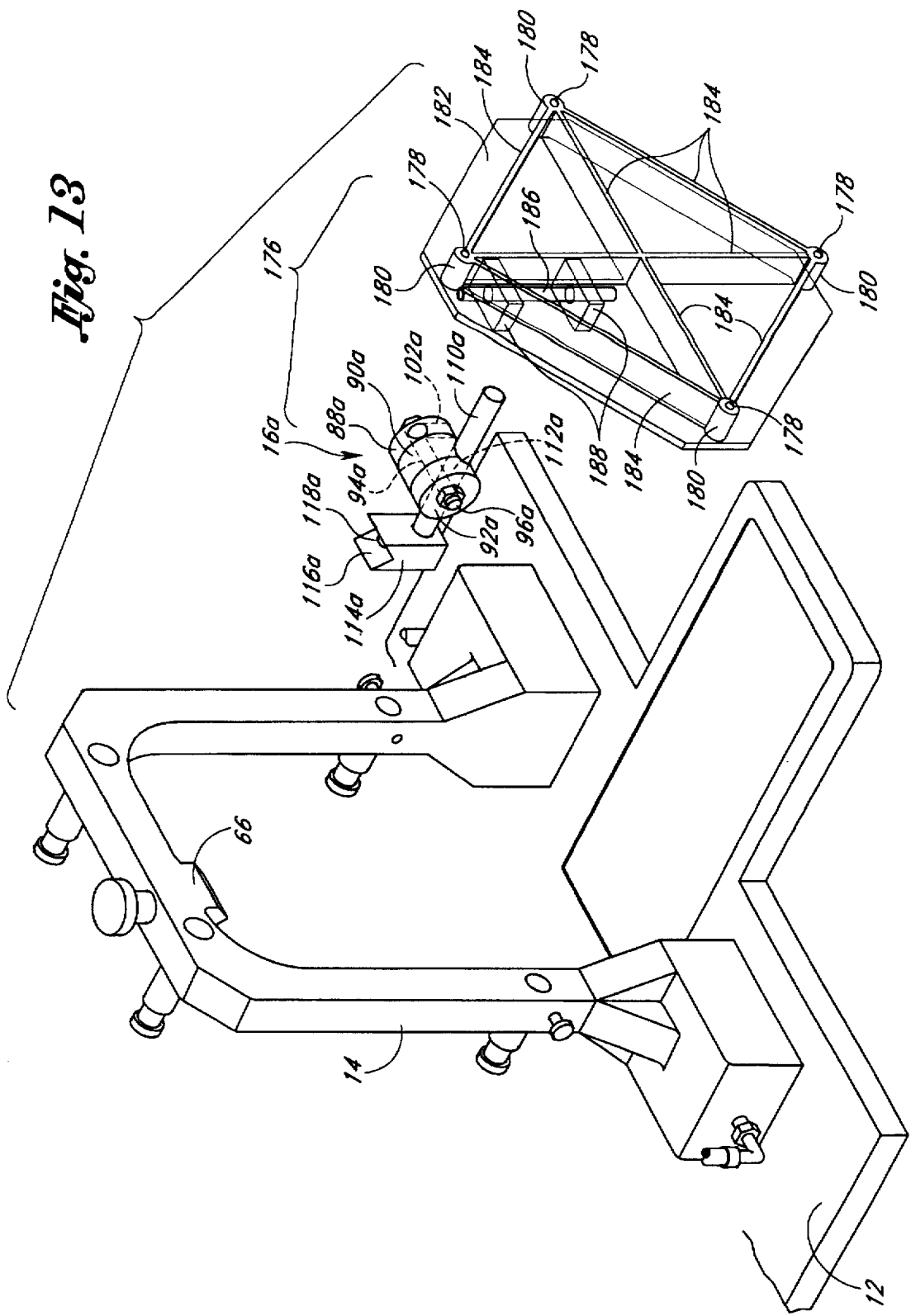
FIG. 13 is an exploded top perspective view of a calibration phantom used with the stereotactic frame of FIG. 1 in accordance with a preferred embodiment of the present invention.

With reference to FIG. 13, a calibration phantom 176 may be used with the above-described stereotactic fixation apparatus 10 to calibrate or align reference planes between diagnostic equipment (e.g., CAT or MRI scanners) and treatment equipment (e.g., a rotatable proton beam gantry). That is, the calibration phantom 176 provides a way for replicating the exact position of the patient's skull relative to the scanning plane of a medical diagnostic device throughout all subsequent treatment phases of the patient's course, as described more fully below.

The calibration phantom 176 attaches to a point on the stereotactic frame 14 or like support to which the detachable fixation device attaches. In the illustrated embodiment, the calibration phantom 176 attaches to the v-shape tang 66. Because the mouthpiece 18 is attached to the frame 14 only at one specific point (i.e., at the tang 66), only the orientation between that point and the scanning plane needs to be replicated in subsequent procedures. The relative orientation between the rest of the frame 14 and/or platform 16 and the scanning plane is irrelevant.

As seen in FIG. 13, the calibration phantom 176 includes a plurality of markers 178 arranged so as to lie in a single plane. The markers 178 also are arranged so as to define at least two intersecting axes. The axes preferably are perpendicular to each other. One of the defined axes desirably lies generally parallel to the platform and the other axis desirably lies generally perpendicular to the platform. In use, as discussed below, the defined axes are aligned with the reference axes of the scanning plane of the diagnostic equipment.

A plurality of posts 180 of equal length desirably support the markers 178 on a flat plate 182 in the desired arrangement. Each post 180 supports one marker 178.

In the illustrated embodiment, the calibration phantom 176 includes four markers 178. The posts 180, which support the markers 178, are located about at the corners of the plate 182, which has a generally square shape. Ribs 184 connect the posts 180 together, generally about the periphery of and diagonally across the plate 182, to strengthen the plate 182 and to interconnect the posts 180.

The markers 178 comprise spherical balls made of a material which is opaque to at least some wavelengths of electromagnetic energy. The markers 178 desirably are made of a material which is easily visible on x-ray and computer tomography (CT) images, such as, for example, ceramic. The markers 178 preferably have a diameter of 3 mm. The spacing between the horizontal set of markers 178 equal about 25 cm (9.84 inches). The spacing between the vertical set of markers 178 equals about the same. It is understood, however, that the size of the markers 178 and the spacing between the markers 178 could be varied to suit the particular requirements of a specific application.

With reference to FIG. 13, a universal joint 16a, similar to that described above, supports the plate 182 on the stereotactic frame 14. Where appropriate, like reference numerals with an "a" suffix have been used to indicate like component between the universal joint 16 used with the mouthpiece 18 and the universal joint 16a used with the calibration phantom 176 for ease of understanding. It also is understood that the present universal joint 16a is configured in accordance with the general description of the universal joint 16 above, except where indicated otherwise.

The universal joint 16a includes a support rod 110a, one end of which is connected to a mount block 114a. The mount block 114a has a generally rectangular block-like shape with a v-shaped notch 116a formed on an upper side. The shape of the notch 116a matches that of the v-shaped tang 66 on the stereotactic frame 14. The mount block 116a also includes a threaded bore 118a to attached the block 116a to the stereotactic frame 14 in a manner similar to that explained above in connection with the universal joint 16 connected to the mouthpiece 18.

In the illustrated embodiment, the universal joint 16a also includes a plurality of adjacent discs 88a, 90a, 92a with a fastener 96a passing through a common central bore 94a of the adjacent discs 88a, 90a, 92a. The fastener 96a joins the discs 88a, 90a, 92a together to form a disc assembly. The fastener 96a can be tightened or loosened so as to move the fastener 96a from an expanded position, in which the discs 88a, 90a, 92a can be rotated relative to one another, to a contracted position, in which the discs 88a, 90a, 92a are locked in a set position.

The mounting rod 110a passes a bore 112a that-extends through the central disc 90a and the second end disc 92a, similar to the universal joint 16 described above. The discs 90a, 92a capture the rod 110a such that the disc assembly can be rotated about the rod 110a when the fastener 96a is loosened. When the fastener 96a is tightened, the central disc 90a and the second end disc 92a clamp against the rod 110a to prevent rotation of the disc assembly about the rod 110a.

The disc assembly also includes another bore 102a that passes through the first end disc 88a in a direction generally normal to the axis of the central bore 94a. The bore 102a is also offset from the center of the disc 88a so as not to intersect with the central bore 94a. In this offset position, a small portion of the bore 102a breaks through the lateral side surface (not shown) of the first disc 88a. The arc of this portion has an angle desirably less than 30°, and more preferably about equal to 10°.

As best seen in FIGS. 14 and 15, the bore 102a between the first disc 88a and the center disc 90a receives a mounting rod 186 attached to the plate 182. The mounting rod 186 has a diameter slightly smaller than the bore 102a so that it can be rotated within the bore 102a. With the mounting rod 186 inserted through the bore 102a, a small portion of the rod 186 extends beyond the flat lateral side surface of the first end disc 88a and lightly contacts the opposing flat lateral surface of the center discs 90a. When the fastener 96a is loosened, the base plate 182 and the mounting rod 186 can rotate relative to the disc assembly, and the first end disc 88a and mounting rod 186 can rotate relative to the center disc 90a. When the fastener 96a is tightened, however, the frictional contact between the first end disc 88a and the center disc 90a prevents the first end disc 88a from rotating relative to the center disc 90a. Likewise, the frictional contact between the center disc 90a and the portion of the mounting rod 186 that extends beyond the lateral side surface of the first end disc 88a prevents the rod 186 from rotating within the bore 102a of the first end disc 88a.

With reference to FIGS. 13 and 14, a pair of support blocks 188 suspend the mounting rod 186 at a position distanced from the base plate 182. The mounting rod 186 lies substantially parallel to the plane defined by markers 178 of the calibration phantom.

In the illustrated embodiment, the support blocks 188 are mounted on a side of the base plate 182 opposite of the side on which the markers 178 are located. The blocks 188 desirably support the mounting rod 186 such that the rod extends in a direction which is generally parallel to the axis defined between the vertical pairing of markers 178. The support blocks 188 also are arranged on the plate 182 so as not to interfere with the universal joint 16a, which supports the plate 182, as the plate 182 is moved to align the markers 178 with the corresponding scanning plane axes, as described below.

As best seen in FIG. 15, the base plate 182 includes an opening 190 which passes though the plate 182 at a location adjacent to the mounting rod 186. In this position, the opening 190 provides a relief through which the support rod 110a of the universal joint passes.

The base plate 182, support posts 180, ribs 184, support blocks 188 and mounting rod 186 desirably are all formed of a material which is generally transparent to the electromagnetic energy used with the particular imaging process, such as, for example, x-ray, CAT, CT or MRI. In an exemplary embodiment, these components are formed of acrylic or like thermoplastic, and are joined together with a suitable bonding agent, such as, for example, methylethylketone (MKE).

Method of Use

When using the stereotactic fixation apparatus 10, a patient lies on the adaptor board 12 in a supine position. The headrest 44 is placed within the recess 42 or 43 on the board 12, and the patient is positioned such that the headrest 44 cradles the posterior side of the patient's skull and supports the nape of the patient's neck.

The stereotactic frame 14 is then placed over the patient and is positioned at a desired location relative to the patient's skull. Specifically, the guide pins 60 of the stereotactic frame 14 are inserted into the hole 58 of the adaptor board 12 at the desired location. The footings 52 of the stereotactic frame 14 sit on top of the adaptor board 12 and compress the O-rings 56 to seal the cavities formed by the recesses 72 of the footings 52 and the top surface of the adaptor board 12. A vacuum supply line 84 (FIG. 2) is connected to the fitting 82 of each footing 52. A vacuum source is then activated to produce a vacuum within the cavity so as to draw the footing 52 against the adaptor board 12. In this manner, the stereotactic frame 14 is removably secured to the adaptor board 12.

The universal joint 16 is attached to the stereotactic frame 14 by inserting the V-shaped groove 116 of the mount block 114 over the V-shaped tang 66 that extends below the horizontal leg 64 of the stereotactic frame 14. When the surfaces of the tang 66 and groove 116 are in contact, the knob 122 is turned to screw the rod 124 attached to the knob 122 into the threaded bore 118 of the mount block 114. The knob 122 is tightened until the mount block 114 is drawn tightly against the tang 66. A set screw or like locking mechanism inserted through an aperture 152 (see FIGS. 6 and 7) in the horizontal leg 64 of the stereotactic frame 14 may be used to lock the rod 124 in place while the mount block 114 is aligned to the tang 66.

As noted above, the universal joint 16 provides the mouthpiece 18 with three degrees rotational freedom in relation to the stereotactic frame 14. The longitudinal distance between the mouthpiece 18 and the stereotactic frame 14 can also be adjusted by sliding the universal joint. 16 along the rod 110. The vertical position of the mouthpiece 18 relative to the stereotactic frame 14 can also be adjusted by sliding the rigid tube 22 through the first bore 102 in the desired direction. In this manner, the mouthpiece 18 can be adjusted relative to the frame 14 during the stereotactic localization procedure.

A vacuum is then applied to the mouthpiece 18 through the port 26 via line 24. The vacuum line 24 is preferably connected to a suction canister 154 (see FIG. 2) which receives any saliva drawn from the patient's mouth, as known in the art.

Vacuum pressure is thus applied to the hard palate through the hole 28 in the upper surface 30 of the acrylic impression 20. The vacuum holds the acrylic impression 20 firmly against the patient's palate and causes the acrylic impression 20 to precisely locate against the patient's dentition and palate.

The highly accurate dental-palatal reproduction and the vacuum thus emplaces and secures the acrylic impression 20 in the same position in the patient's mouth for each diagnostic procedure and subsequent treatments. Because the skull is rigidly connected to the upper dentition and alveolar ridge, the repeatable positioning of the acrylic impression 20 enables one to repeatedly position the patient's head.

The orientation of the mouthpiece is adjusted with the stereotactic fixation apparatus configured in accordance with the above description and the mouthpiece 18 secured in the patient's mount by the applied vacuum. Through the range of rotational and linear adjustment provided by the universal joint 16, the patient's skull can be adjust to rest in a comfortable position. The universal joint 16 is then locked to form a mechanical memory of the patient's skull relative to the attachment point (i.e., the v-shape tang 66) on the stereotactic frame 16.

As noted above, the present stereotactic fixation apparatus includes a quick release mechanism which enables the patient to quickly dislodge the restraint of the stereotactic frame 14 and mouthpiece 18 in exigent circumstances (e.g., choking, vomiting, etc.). The patient simply presses the switch 32 in such exigent circumstances and sits upright. The patient can then dislodge the mouthpiece 18 from his or her mouth. As discussed above, the vacuum control system 34 disconnects the source of vacuum from the mouthpiece port 26 and the ports 76 of the stereotactic frame 14. The patient can then overcome the residual vacuum pressure by normal movement.

The interlock subsystem 150 of the central system 34 detects the activation of the patient's switch 32 and disables the associated medical device. Imaging or treatment of the patient stops. The interlock system 150 thus prevents exposure of non-target site tissue to any radiation emitted by the diagnostic or treatment apparatus. As noted above, the interlock subsystem 150 also detects the absence of vacuum hold-down pressure at the frame/platform interfaced 72 or at the acrylic impression 20. The interlock subsystem 150 likewise will disable the associated treatment or diagnostic device if it defects an absence of a vacuum at either of these locations.

As noted above, the orientation of the scanning plane of the medical diagnostic or treatment equipment relative to the mouthpiece 18 desirably is consistent throughout all planing and treatment phases of the patient's course, even though all phases may not be performed using the same equipment, nor performed at the same facility. The precise orientation between the mouthpiece 18 and the scanning plane enables exact replicate of the position of the patient's skull relative to the scanning plane.

The mouthpiece 18 and attached universal joint 16 will accompany the patient throughout all planning and treatment phases of the patient's course after the initial planning session in which the orientation of the mouthpiece 18 is established. This ensures that there is no variation in this apparatus from facility to facility. It is contemplated, however, that the platform 12 and stereotactic frame 14 will not. The stereotactic frame 14 and platform 12 remain with the particular medical diagnostic or treatment equipment.

In all subsequent treatment procedures, the orientation of the support apparatus (e.g., the stereotactic frame 14) relative to a corresponding reference plane must be calibrated with the orientation of the support apparatus (e.g., stereotactic frame 14) used in the initial planning secession relating to the "primary" scanning plane in order to precisely replicate the planned position of the patient's skull in stereotactic space. In the illustrated embodiment, the position of the V-shaped tang 66 relative to the corresponding treatment reference plane must be calibrated with the orientation of the tang 66 used in the initial planning stage with relative to the primary scanning plane.

As noted above, the calibration phantom 176 can be used to calibrate the orientation of a skull immobilization device (e.g., the mouthpiece 18) in subsequent procedures. The calibration phantom 176 initially is fixed to the support apparatus used with the initial diagnostic equipment (e.g., a MRI or CT scanner). In the illustrated embodiment, the universal joint 16a is attached to the stereotactic frame 14 by inserting the V-shaped groove 116a of the mount block 114a over the V-shaped tang 66 that extends below the horizontal leg 64 of the stereotactic frame 14. When the surfaces of the tang 66 and groove 116a are in contact, the knob 122 is turned to screw the rod 124 attached to the knob 122 into the threaded bore 118a of the mount block 114. The knob 122 is tightened until the mount block 114a is drawn tightly against the tang 66. A set screw or like locking mechanism inserted through an aperture 152 (see FIGS. 6 and 7) in the horizontal leg 64 of the stereotactic frame 14 may be used to lock the rod 124 in place while the mount block 114a is aligned to the tang 66.

The calibration phantom 176 is aligned with the reference axes of the scanning plane of the diagnostic equipment. Where the initial planning secession involves computer tomography (CT) imaging, the CT device produces an image of the calibration phantom markers 178 on its visual display. The CT device also projects reference axes over the image of the calibration phantom 176. A technician rotates the plate 182 of the calibration phantom 176 with the universal joint 16a loosened until all markers 178 appear in one scanning plane and are parallel with the prime reference axes of the CT device. The technician, locks the universal joint 16a once the markers 176 are aligned with the CT reference axes to form a mechanical memory of the orientation of the tang 66 relative to the CT scanning plane.

The calibration phantom 176 later is transported to a treatment room to orient the support apparatus used with the treatment device so as to replicate the exact orientation between the support apparatus and the planar axes of the treatment device that existed between the support apparatus and the primary planar axes of the diagnostic device during the initial planning procedure.

The calibration phantom 176 is attached to the support apparatus used with the treatment device in a manner similar to that described above. An imaging device (i.e., x-ray machine) used with the treatment device (e.g., a rotatable proton beam gantry) is used to produce an image of the calibration phantom 176 attached to the support apparatus (e.g., the stereotactic frame 14). The imaging device also projects reference axes over the image of the calibration phantom 176. Images desirably are taken from orthogonal directions.

A technician adjusts the support apparatus in response to the images to align the markers 178 of the calibration phantom 176 with the reference axes of the treatment device. In the illustrated embodiment, the technician can shim the platform 12 in order to move the tang 66 of the stereotactic frame 14 until the markers 178 align with the reference axes of the treatment device.

Use of the calibration phantom 176 in the above described manner ensures that the location of the attachment point on the support apparatus (e.g., the tang 66 on the stereotactic frame 14) relative to the scanning plane axes is consistent with each piece of medical equipment used throughout the patient's course. As such, the orientation of the stereotactic fixation device (e.g., the mouthpiece 18), which attaches to the support apparatus attachment point (e.g., the tang) relative to the treatment reference axes remains constant from procedure to procedure. In this manner, the present stereotactic fixation system can be used to precisely and reproducible position the patient's skull throughout all diagnostic, planning and treatment stages, even when such procedures are performed at different facilities.

Additional Embodiment

Figure 16:
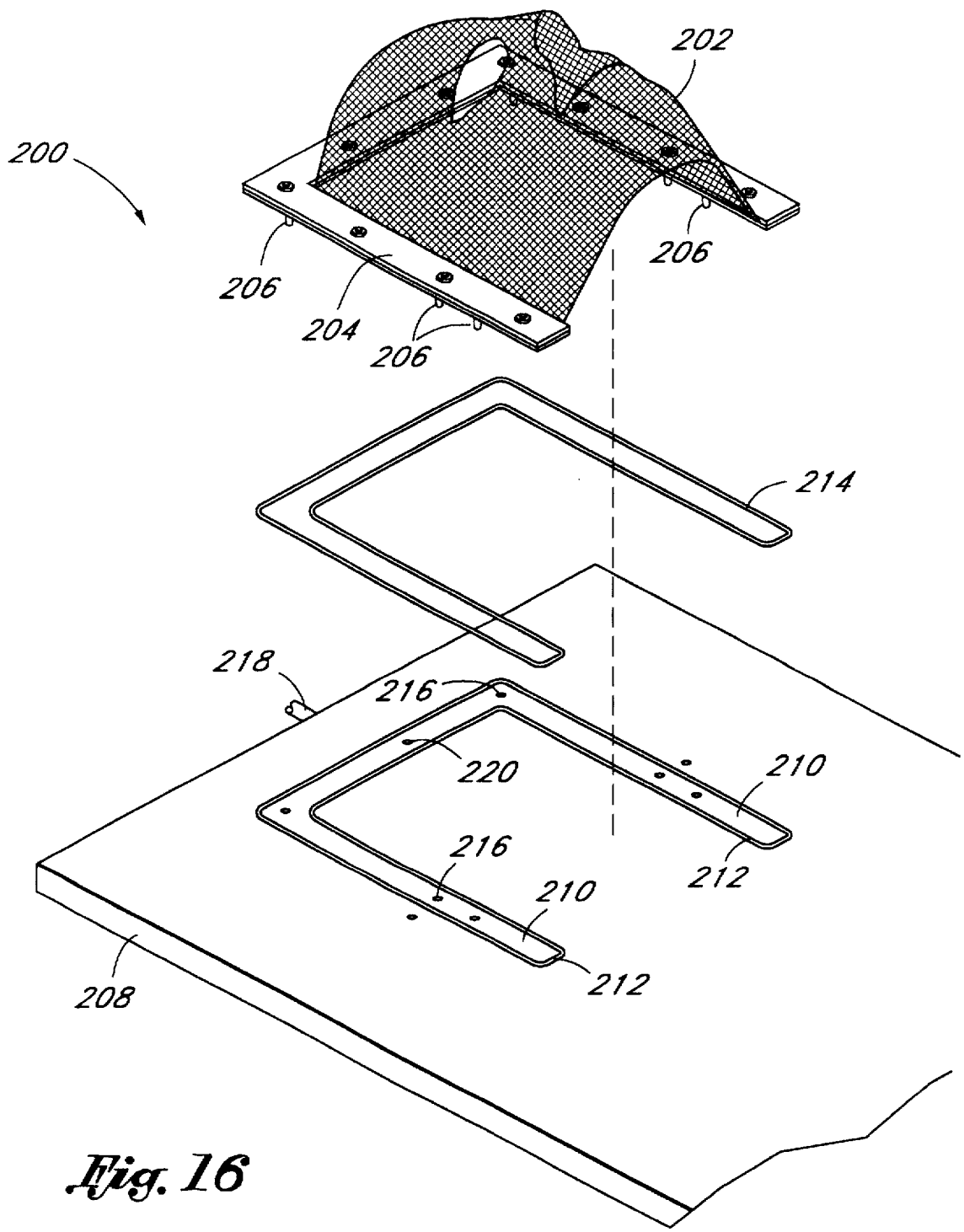
FIG. 16 is an exploded top perspective view of a stereotactic fixation apparatus in accordance with a second preferred embodiment of the present invention.

With reference to FIG. 16, there is provided an additional fixation apparatus 200 configured in accordance with another preferred embodiment of the present invention. The fixation apparatus 200 includes a facial mask 202 formed of a thermoplastic material. The thermoplastic material is heated to a degree in which the material is pliable, and is then placed over the anterior portion of the patient's skull. The material is molded to the contours of the patient's anterior features and is allowed to harden in this configuration. In this manner, the facial mask 202 forms an impression of the patient's facial features.

The facial mask 202 is attached to a mounting frame 204 by conventional means. The mounting frame generally has a U-shape of a sufficient size to surround the periphery of a patient's head. The mounting frame 204 also includes guide pins 206 which are used to position the mounting frame 204, as discussed below.

The fixation apparatus 200 also includes an adaptor board 208. The adaptor board 208 generally has a rectangular shape sized to support an adult body in a supine position. The adaptor board 208 includes a U-shaped recess 210 and a groove 210 that outlines the periphery of the recess 210. The groove 212 and recess 210 are sized smaller than the mounting frame 204 such that the mounting frame 204 completely covers the groove 212 and recess 210.

The adaptor board 208 further includes a seal 214 having a circular cross-sectional shape and configured to sit within the groove 212. The seal 214 desirably has a diameter larger than the depth of the corresponding groove 212, such that the seal 214 extends above the surface of the adaptor board 208 when seated within the groove 212.

The adaptor board 208 further includes alignment holes 216 which cooperate with the guide pins 206 on the mounting frame 204. The alignment holes 216 are positioned with respect to the recess 210 and the groove 212 so as to position the mounting frame 204 over the seal 214 and the recess 210. In this manner, a substantially sealed cavity is formed between the mounting frame 204 and adaptor board 208 when the mounting frame 204 covers the recess 210.

The adaptor board 208 also includes a port 218 connected to a channel (not shown) which extends through the adaptor board 208 and opens into the recess 210 through an aperture 220. The port 218 is adapted to connect to a source of vacuum.

When the fixation apparatus 200 is used in radiotherapy or like medical procedures, the patient is placed on the adaptor board 208 in the supine position. The face mask 202 is then placed over the patient, and the patient's skull is oriented within the face mask 202 such that the face mask 202 sits directly against the anterior features of the patient's skull. The guide pins 206 of the mounting frame 204 are then inserted into the alignment holes 216 of the adaptor board 208 to properly position the mounting frame 204 over the recess 210. The port 218 in the adaptor board 208 is then connected to a vacuum source so as to apply vacuum pressure within the recess 210. The vacuum holds the mounting frame 204 against the adaptor board 208.

The fixation apparatus 200 may also include the patient-activated quick release mechanism discussed above. This quick-release mechanism allows the patient to disconnect the port 218 from the source of vacuum upon activation of the switch 34 (FIG. 2). When the vacuum is disconnected from the port 218, the patient can remove the mounting frame 204 from the adaptor board 208. It should be noted that the vacuum system will inherently have slight leaks such that a vacuum lock is not formed between the mounting frame 204 and the adaptor board 208. Thus, the patient will be able to overcome any residual vacuum pressure by lifting his or her head off of the adaptor board 208.

Although this invention has been described in terms of a certain preferred embodiment, other embodiments apparent to those of ordinary skill in the art are also within the scope of this invention. Accordingly, the scope of the invention is intended to be defined only by the claims which follow.

What is claimed is:

1. A calibration phantom used to replicate the position of a stereotactic immobilization device relative to a scanning plane of a medical device, the scanning plane having a pair of intersecting axes for reference purposes, said stereotactic immobilization device releasably attaching to at least one point on a support apparatus used with the medical device, said calibration phantom comprising:

a plurality of markers located in a plane and defining at least two intersecting axes; and a support coupled to said markers, said support configured to releasably attach to the support apparatus in place of the stereotactic immobilization device said support also configured to releasably attach to the same point on the support apparatus that the stereotactic immobilization device is releasably attached.

2. The calibration phantom of claim 1, wherein said support is configured to suspend said markers away from the support apparatus.

3. The calibration phantom of claim 2, wherein said support comprises an adjustable coupling that provides at least three degrees of rotational movement of said markers relative to the support apparatus and at least two degrees of linear movement of said markers relative to the support apparatus so as to align said axes defined by said markers with axes of a scanning plane of the medical device.

4. The calibration phantom of claim 3, wherein said coupling includes a releasable locking mechanism which selectively prevents said markers from moving relative to the support apparatus.

5. The calibration phantom of claim 1, wherein said support additionally comprises a base plate which carries said markers.

6. The calibration phantom of claim 1, wherein said markers are formed of a material which is visible on x-ray and computer tomography images.

7. A calibration phantom used to replicate the position of a stereotactic immobilization device relative to a scanning plane of a medical device, the scanning plane having a pair of intersecting axes for reference purposes, said stereotactic immobilization device releasably attaching to at least one point on a support apparatus used with the medical device, said calibration phantom comprising:

a plurality of markers located in a plane and defining at least two intersecting axes; and a support coupled to said markers, said support configured to releasably attach to the support apparatus at the same point on the support apparatus that the stereotactic immobilization device is releasably attached wherein said support comprises an adjustable coupling that provides at least three degrees of rotational movement of said markers relative to the support apparatus and at least two degrees of linear movement of said markers relative to the support apparatus so as to align said axes defined by said markers with the axes of the scanning plane of the medical device.

8. The calibration phantom of claim 7, wherein said support is configured to suspend said markers away from the support apparatus.

9. The calibration phantom of claim 8, wherein said coupling includes a releasable locking mechanism which selectively prevents said markers from moving relative to the support apparatus.

10. The calibration phantom of claim 7, wherein said support additionally comprises a base plate which carries said markers.

11. The calibration phantom of claim 7, wherein said markers are formed of a material which is visible on x-ray and computer tomography images.

12. The calibration phantom of claim 7, wherein said coupling comprises a connector having a groove that fits over a tang at said point of said support apparatus.

13. An apparatus for use with a medical device having a scanning plane, comprising:

a support apparatus including an attachment point;

a calibration phantom including at least two markers located in a common plane and defining at least two axes, said calibration phantom configured to releasably attach to said attachment point so that said markers are positioned in the scanning plane of the medical device;

a stereotactic immobilization device configured to releasably couple to said attachment point in place of said calibration phantom so that said stereotactic immobilization device orients in said scanning plane in a position corresponding to the position of said calibration phantom in said scanning plane.

14. The calibration phantom of claim 13, wherein said calibration phantom includes a support comprising an adjustable coupling that provides at least three degrees of rotational movement of said markers relative to the support apparatus and at least two degrees of linear movement of said markers relative to the support apparatus so as to align said axes defined by said markers with axes of the scanning plane of the medical device.

15. The calibration phantom of claim 14, wherein said coupling includes a releasable locking mechanism which selectively, prevents said markers from moving relative to the support apparatus.

16. The calibration phantom of claim 14, wherein said support additionally comprises a base plate which carries said markers.

17. The calibration phantom of claim 13, wherein said markers are formed of a material which is visible on x-ray and computer tomography images.

18. A method of using a calibration phantom to replicate the position of a stereotactic immobilization device relative to a first scanning plane of a first medical device to a second scanning plane in a second medical device, the scanning planes each having a pair of intersecting axes for reference purposes, the stereotactic immobilization device releasably attaching to at least one point on a support assembly used with either the first or the second medical devices, the method comprising:

attaching the calibration phantom to a first support frame associated with a first medical device;

orientating the calibration phantom with respect to the first support frame so that markers on the calibration phantom correspond to axes on the first scanning plane;

removing the calibration phantom from the first support frame;

attaching the calibration phantom to a second support frame associated with a second medical device;

orienting the second support frame so that the markers of the calibration phantom correspond to axes on the second scanning plane so that the position of the calibration phantom in the second scanning plane corresponds to the position of the calibration phantom in the first scanning plane;

replacing the calibration phantom on the second support frame with the stereotactic immobilization device so that when the stereotactic immobilization device is attached on the second support frame, the position of the stereotactic immobilization device in the second scanning plane corresponds to the position of the calibration phantom in the second scanning plane.

19. The method of claim 18, wherein orientating the calibration phantom with respect to the first support frame comprises manipulating a connector interconnecting the calibration phantom to the first support frame that provides at least three degrees of rotational movement of said markers relative to the first support frame and at least two degrees of linear movement of said markers relative to the first support frame so as to align axes defined by said markers with axes of the first scanning plane.

20. The method of claim 19, wherein orientating the calibration phantom with respect to the first support frame additionally comprises locking the position of said connector to prevent said markers from moving relative to said first support frame.

21. The method of claim 20, wherein attaching the phantom to a second support frame comprises attaching said connector to a first point on said second support frame.

22. The method of claim 21, wherein replacing the calibration phantom on the second support frame with the stereotactic immobilization device comprises attaching the stereotactic immobilization device to said first point on said second support frame.

* * * * *